US007491499B2

(12) United States Patent
Sawa

(10) Patent No.: US 7,491,499 B2
(45) Date of Patent: Feb. 17, 2009

(54) METHOD FOR DIAGNOSING OR PREDICTING SUSCEPTIBILITY TO PSYCHIATRIC DISORDERS

(75) Inventor: Akira Sawa, Baltimore, MD (US)

(73) Assignees: The Johns Hopkins University, Baltimore, MD (US); Rusk Intellectual Reserve AG, Zug (CH)

( * ) Notice: Subject to any disclaimer, the term of this patent is extended or adjusted under 35 U.S.C. 154(b) by 52 days.

(21) Appl. No.: 11/043,959

(22) Filed: Jan. 28, 2005

(65) Prior Publication Data

US 2005/0255500 A1 Nov. 17, 2005

Related U.S. Application Data

(60) Provisional application No. 60/539,900, filed on Jan. 28, 2004.

(51) Int. Cl.
*G01N 33/53* (2006.01)
*G01N 33/567* (2006.01)
*G01N 33/542* (2006.01)
*G01N 33/566* (2006.01)

(52) U.S. Cl. ............... 435/7.1; 435/7.21; 435/7.8; 435/7.9; 435/7.92; 436/501; 436/503

(58) Field of Classification Search ............... None
See application file for complete search history.

(56) References Cited

OTHER PUBLICATIONS

Devon et al., 2001, Psychiatric Genetics, 11, pp. 71-78.*
Tadafumi Kato, Neurosci. Res., 2001, 40, pp. 105-113.*
Kamiya et al., Soc. Neurosci Abstarcts, 2001, vol. 27, No. 1, pp. 1493.*
Ozeki et al., Soc. Neurosci Abstarcts, 2001, vol. 27, No. 1, pp. 1493.*
James et al., Soc. Neurosci Abstarcts, 2003, Abstract No. 312.4.*
Fridoon J. Ahmad, Christophe J. Echeverri, Richard B. Vallee, and Peter W. Baas; Cytoplasmic Dynein and Dynactin Are Required for the Transport into the Axon; The Journal of Cell Biology, vol. 140, No. 2, Jan. 26, 1998, pp. 391-401.
D.H.R. Blackwood, A. Fordyce, M.T. Walker, D.M. St. Clair D.J. Porteous, and W.J. Muir; Schizophrenia and Affective Disorders-Cosegregation with a Translocation at Chromosome 1q42 That Directly Disrupts Brain-Expressed Genes: Clinical and P300 Findings in a Family; Am. J. Genet. 69:428-433, 2001.
N.J. Brandon, E.J. Handford, I. Schurov, J.-C. Rain, M. Pelling, B. Duran-Jimeniz, L.M. Camargo, K.R. Oliver. D. Heher, M.S. Shearman, and P.J. Whiting; Disrupted in Schizophrenia 1 and Nudel form a neurodevelopmentally regulated protein complex: implications for schizophrenia and other major neurological disorders; Mo. Cell. Neuorosci. 25 (2004) 42-55.
Vivian G. Cheung, Laura K. Conlin, Teresa M. Weber, Melissa Arcaro, Kuang-Yu Jen, Michael Morley and Richard S. Spielman; Natural variation in human gene expression assessed in lymphoblastoid cells; nature genetics, vol. 33, Mar. 2003, pp. 422-425.

Joseph T. Coyle, and Ronald S. Duman; Finding the Intracellular Signaling Pathways Affected by Mood Disorder Treatments; Neuron, vol. 38, 157-160, Apr. 24, 2003.
Lee Crews and Dale Hunter; Neurogenesis in the Olfactory Epithelium; Perspectives on Developmental Neurobiology, 1994, Vo. 2, No. 2, pp. 151-161.
David Curtis, Gursharan Kalsi, Jon Brynjolfsson, Melvin McInnis, Jane O'Neill, Ciaran Smyth, Eamonn Moloney, Patrice Murphy, Andrew McQuillin, Hannes Petursson and Hugh Gurling; Genome scan of pedigrees multiply affected with bipolar disorder provides further support for the presence of a susceptibility locus on chromosome 12q23-q24, and suggests the presence of additional loci on 1p and 1q; Psychiatric Genetics 2003, vol. 13, No. 2, pp. 77-84.
Sevilla D. Detera-Wadleigh, Judith A. Badner, Wade H. Berrettini, Takeo Yoshikawa, Lynn R. Goldin, Gordon Turner, Denise Y. Rollins, Tracy Moses, Alan R. Sanders, Jayaprakash D. Karkera, Isa E. Esterlig, Jin Zeng, Thomas N. Ferraro, Juliet J. Guroff, Diane Kazuba, Mary E. Maxwell, John I. Nurnberger, Jr., and Elliot S. Gershon; A high-density genome scan detects evidence for a bipolar-disorder susceptibility locus on 13q32 and other potential loci on 1q32 and 18p11.2; Proc. Natl. Acad. Sci. USA, vol. 96, pp. 5604-5609, May 1999, Genetics.
J Ekelund, W Hennah, T Hiekkalinna, A Parker, J Meyer, J Lönnqvist, and L Peltonen; Replication of Iq42 linage in Finnish schizophrenia pedigrees; Molecular Psychiatry (2004) 9, pp. 1037-1041.
Schahram Akbarian, MD, PhD, William E. Bunney, Jr., MD, Steven G. Potkin, MD, Sharon B Wigal, PhD, Jennifer O. Hagman, MD, Curt A. Sandman, PhD, Edward G. Jones, MD, PhD; Altered Distribution of Nicotinamide-Adenine Dinucleotide Phosphate-Diaphorase Cells in Frontal Lobe of Schizophrenics Implies disturbances of Cortical Development; Arch Gen Psychiatry—vol. 50, Mar. 1993, pp. 169-177.
Jesper Ekelund, Liris Hovatta Alex Parker, Tina Paunio, Teppo Varilo, Rory Martin, Johanna Suhonen, Pekka Ellonen, Gayun Chan, Janet S. Sinsheimer, Eric Sobel, Hannu Juvonen, Ritva Arajärvi, Timo Partonene, Jaana Suvisaari, Jouko Lönnqvist, Joanne Meyer, and Leena Peltonen; Chromosome 1 loci in Finnish schizophrenia families; Human Molecular Genetics, 2001, vol. 10, No. 15. pp. 1611-1617.
Effat S. Emamian, Diana Hall, Morris J Birnbaum, Maria Karayiorgou & Joseph A Gogos; Convergent evidence for impaired AKT1-GSK3β signaling in schizophrenia; Nature Genetics, vol. 36, No. 2, Feb. 2004, pp. 131-137.
Albert I. Farbman; Developmental biology of olfactory sensory neuron; Seminars in Cell Biology, vol. 5, 1994; pp. 3-10.
F. Féron, C. Perry, M.H. Hirning, J. McGrath, A. Mackay-Sim; Altered adhesion, proliferation and death in neural cultures from adults with schizophrenia; Elsevier, schizophrenia Research 40 (1999) 211-218.

(Continued)

*Primary Examiner*—Olga N. Chernyshev
(74) *Attorney, Agent, or Firm*—Sughrue Mion, PLLC

(57) ABSTRACT

The present invention provides a method for diagnosing or predicting susceptibility to a psychiatric disorder in an individual, which comprises confirming molecular diversity and/or subcellular distribution of DISC 1 in the cell from the individual. In addition, a novel risk haplotype of DISC1 for psychiatric disorder is also provided.

5 Claims, 13 Drawing Sheets

OTHER PUBLICATIONS

Stacey B. Gabriel, Stephen F. Schaffner, Huy Nguyen, Jamie M. Moore, Jessica Roy, Bredan Blumenstiel, John Higgins, Matthew DeFelice, Amy Lochner, Maura Faggart, Shau Neen Liu-Cordero, Charles Rotimi, Adebowale Adeyemo, Richard Cooper, Ryk Ward, Eric S. Lander, Mark J. Daly, David Altschuler; The Structure of Haplotype Blocks in the Human Genome; Science, vol. 296, Jun. 21, 2002, pp. 2225-2229.

Yongjun Gu, Hiroaki Misonou, Toru Sato, Naoshi Dohmae, Koji Takio, and Yasuo Ihara; Distinct Intramembrane Cleavage of the β-Amyloid Precursor Protein Family Resembling γ-Secretase-like Cleavage of Notch; The Journal of Biological Chemistry, vol. 276, Issue of Sep. 21, pp. 35235-35238, 2001.

P J Harrison and D R Weinberger; Schizophrenia genes, gene expression, and neuropathology: on the matter of their convergence; Molecular Psychiatry (2005) 10, 40-68.

William Hennah, Teppo Varilo, Marjo Kestila, Tiina Paunio, Ritva Arajärvi, Jari Haukka, Alex Parker, Rory Martin, Steve Levitzky, Timo Partonen, Joanne Meyer, Jouko Lönnqvist, Leena Peltonen and Jesper Ekelund; Haplotype transmission analysis provides evidence of association for DISC1 to schizophrenia and suggests sex-dependent effects; Human Molecular Genetics, 2003, vol. 12, No. 23, pp. 3151-3159.

Colin A. Hodgkinson, David Goldman, Judith Jaeger, Shalini Persaud, John M. Kane, Robert H. Lipsky, and Anil K. Malhotra; Disrupted in Schizophrenia 1 (DISC1): association with Schizophrenia, Schizoaffective Disorder, and Bipolar Disorder; Am. J. Genet. 75:862-872, 2004.

Steve Horvath, Xin Xu and Nan M Laird; The family based association test method: strategies for studying genotype-phenotype associations; European Journal of Human Genetics (2001) 9, 301-306.

Nancy C. Andrews and Douglas V. Faller; A rapid micropreparation technique for extraction of DNA-binding proteins from limiting numbers of mammalian cells; Nucleic Acids Research, vol. 19, No. 9, 2499 (1991).

Xianxin Hua, Juro Sakai, Michael S. Brown, and Joseph L. Goldstein; Regulated Cleavage of Sterol Regulatory Element Binding Proteins Requires Sequences on Both Sides of the Endoplasmic Reticulum Membrane; The Journal of Biological Chemistry, vol. 271, No. 17, Issue of Apr. 26, pp. 10379-10384, 1996.

H-G Hwu, C-M Liu, CS-J Fann, W-C Ou-Yang and SF-C Lee; Linkage of schizophrenia with chromosomes 1q loci in Taiwanese families; Molecular Psychiatry (2003) 8, 445-452.

R. James, R.R. Adams, S. Christie, S.R. Buchanan, D.J. Porteous, and J.K. Millar; Disrupted in Schizophrenia 1 (DISC1) is a multicompartmentalized protein that predominantly localizes to mitochondria; Molecular and Cellular Neuroscience 26 (2004), pp. 112-122.

Michael B. Knable; Schizophrenia and bipolar disorder: findings from studies of the Stanley Foundation Brain Collection; 1999 Elsevier Science B.V., Schizophrenia Research 39 (1999) 149-152.

Phil OK Koh, PhD, Clare Bergson, PhD, Ashiwel S. Undie, PhD, Patricia S. Goldman-Rakic, PhD, Michael S. Lidow,PhD; Up-regulation of the D1 Dopamine Receptor-Interacting Protein, Calcyon, in Patients With Schizophrenia; Arch Gen Psychiatry/Vo. 60, Mar. 2003, pp. 311-319.

Phil OK Koh, Ashiwel S. Undie, Nadine Kabbani, Robert Levenson, Patricia S. Goldman-Rakic and Michael S. Lidow; Up regulation of neuronal calcium sensor-1(NCS-1) in the prefrontal cortex of schizophrenic and bipolar patients; PNAS/ Jan. 7, 2003, vol. 100, No. 1, 313-317.

Morten L. Dringelbach, Edmund T. Rolls; The functional neuroanatomy of the human orbitofrontal cortex: evidence from neuroimaging and neuropsychology; Progress in Neurobioloy 72 (2004) 341-372.

Edythe F. London, Monique Ernst, Steven Grant, Katerine Bonson and Aviv Weinstein; Orbitofrontal Cortex and Human Drug Abuse: Function Imaging; Cerebral Cortex Mar. 2000; 10:334-342; 1047-3211/00.

Lei Ma, Yuan Liu, Betty Ky, Paul J. Shughrue, Christopher P. Austin, and Jill A. Morris; Cloning and Characterization of Disc1, the Mouse Ortholog of DISC1 (Disrupted-in-Schizophrenia 1); Genomics, vol. 80, No. 6, Dec. 2002, pp. 662-672.

S MacGregor, PM Visscher, SA Knott, P Thomson, DJ Porteous, JK Millar, RS Devon, D Blackwood and WJ Muir; A genome scan and follow-up study identify a bipolar disorder susceptibility locus on chromosome 1q42; Molecular Psychiatry (2004) 9, 1083-1090.

Steven E. Arnold, MD; Li-Ying Han, MS; Paul J. Moberg, PhD; Bruce I. Teretsky, MD; Raquel E. Gur, MD, PhD; John Q. Trojanowski, MD,PhD; Chang-Gyu Hahn, MD, PhD; Dysregulation of Olfactory Receptor Neuron Linage in Schizophernia; Arch Gen Psychiatry/vol. 58, Sep. 2001, pp. 829-835.

MG McInnis, T-H Lan, VL Willour, FJ McMahon, SG Simpson, AM Addington, DF MacKinnon, JB Potash, AT Mahoney, Jchellis, Y Huo, T Swift-Scanlan, H Chen, R Koskela, O Colin Stine, KR Jamison, P Holmans, SE Folstein, K Ranade, C Friddle, D Botstein, T Marr, TH Beaty, P Zandi and J Raymond DePaulo; Genome-wide scan of bipolar disorder in 65 pedigrees: supportive evidence for linkage a 8q24, 18q22, 4q32, 2p12, and 13q12; Molecular Psychiatry (2003) 8, 288-298.

J. Kirsty Millar, Sheila Christie, and David J. Porteous; Yeast two-hybrid screens implicate DISC1 in brain development and function; 2003 Elsevier Inc., Science Direct, Biochemical and Biophysical Research Communications 311 (2003) 1019-1025.

J. Kirsty Millar, Julie C. Wilson-Aanon, Susan Anderson, Shelia Christie, Martin S. Taylor, Colin A.M. Semple, Rebecca S. Devon, David M. St Clair, Walter J. Muir, Douglas H.R. Blackwood and David J. Porteous; Disruption of two novel genes by a translocation co-segregating with schizophrenia; Human Molecular Genetics, 200, vol. 9, No. 9, 1415-1423.

K Miyoshi, A. Honda, K Baba, M Taniguchi, K Oono, T Fujita, S Kuroda, T Katayama and M Tohyama; Disrupted-In Schizophrenia 1, a candidate gene for schizophrenia, participates in neurite outgrowth; Molecular psychiatry (2003) 8, 685-694.

Paul J. Moberg, PhD., Rachel Agrin, B.S., Raquel E. Gur, M.D., PhD., Ruben C. Gur, PhD., Bruce I. Turetsky, M.D., and Richard L. Doty, PhD.; Olfactory Dysfunction in Schizophrenia: A Qualitative and Quantitative Review; Nueropsychopharmacology 1999-vol. 21, No. 3, pp. 325-340.

Mohammed Moudjou and Michel Bornens; Method of Centrosomes Isolation from Cultured Animal Cells; Cell Biology: A Laboratory Handbook, Second Edition, vol. 2, pp. 111-119.

Michael Morley, Cliona M. Moloney, Teresa M. Weber, James L. Devlin, Kathryn G. Ewens, Richard S. Spielman & Vivian G. Cheung; Genetic analysis of genome-wide variation in human gene expression; Nature/ vol. 430/ Aug. 12, 2004/ pp. 743-747.

Jill A. Morris, Geeta Kandpal, Lei Ma and Christopher P. Austin; DISC1 (Disrupted-In-Schizophrenia 1) is a centrosome-associated protein that interacts with MAPIA, MIPT3, ATF4/5, and NUDEL: regulation and loss of interaction with mutation; Human Molecular Genetics, 2003, vol. 12, No. 13, pp. 1591-1608.

Eiichiro Nagata, Akira Sawa, Christopher A. Ross, and Solomon H. Snyder; Autophagosome-like vacuole formation in Huntington's disease lymphoblasts; Molecular Neuroscience, vol. 15, No. 8, Jun. 2004, pp. 1325-1328.

C.P. Austin, B.Ky, L. Ma, J.A. Morris, and P.J. Sughrue; Expression of Disrupted-In-Schizophrenia-1, a Schizophrenia-Associated Gene, is prominent in the Mouse Hippocampus Throughout Brain Development; Neuroscience 124 (2004) 3-10.

Kazunori Nakajima, Katsuhiko Mikohiba, Takaki Miyata, Chikako Kudo, and Masaharu Ogawa; disruption of hippocampal development in vivo by CR-50 mAb against Reelin; Proc. Natl. Acad. Sci. USA vol. 94, pp. 8196-8201, Jul. 1997, pp. 8196-8201.

Martin Niethammer, Deanna S. Smith, Ramses Ayala, Junmin Peng, Jane Ko, Ming-Sum Lee, Maria Morabito, and Li-Huei Tsai; NUDEL Is a Novel Cdk5 Substrate that Associates with LIS1 and Cytoplasmic Dynein; Neuron, vol. 28, 697-711, Dec. 2000.

Hitoshi Niwa, Ken-Ichi Yamamura and Jun-Ichi Miyazaki; Efficient selection for high-expression transfectants with a novel eukaryotic vector; 1991 Elsevier Science Publishers, Gene, 108 (1991) 193-200.

Yuji Ozeki, Toshifumi Tomoda, John Kleiderlein, Atsushi Kamiya, Lyuda Bord, Kumiko Fujii, Masako Okawa, Naoto Yamada, Mary E. Hatten, Solomon H. Synder, Christopher A. Ross, and Akira Sawa; Disrupted-in-Schizophrenia-1 (DISC-1): Mutant truncation prevents binding to NudE-like (NUDEL) and inhibits neurite outgrowth; PNAS/ Jan. 7, 2003/ vol. 100/ No. 1/ 289-294.

Alexander V. Panov, Claire-Anne Gutekunst, Blair R. Leavitt, Michael R. Hayden, James R. Burke, Warren J. Strittmatter, and J. Timothy Greenamyre; Early mitochondrial calcium defects in Huntington's disease are a direct effect of polyglutamines; nature neuroscience, vol. 5, No. 8, Aug. 2002, pp. 731-736.

Linda J. Porrino and David Lyons; Orbital and Medical Cortex and Psychostimulant Abuse: Studies in Animal Models; Cerebral Cortex, Mar. 2000; 10:326-333; 1047-3211/00.

T.H. Rabbitts; Chromosomal translocations in human cancer; Nature, vol. 372, Nov. 10, 1994, pp. 143-149.

Orly, Reiner, Romeo Carrozzo, Ying Shen, Manfred Wehnert, Fabrizia Faustinella, William B. Dobyns, C. Thomas Caskey & David H. Ledbetter; Isolation of a Miller-Dieker lissencephaly gene containing G protein β-submit-like repeats; Nature, vol. 364, Aug. 19, 1993, pp. 717-721.

Edmund T. Rolls; The Orbitofrontal Cortex and Reward; Cerebral Cortex Mar. 2000; 10:284-294; 1047-3211/00.

M Elizabeth Ross and Christopher A Walsh; Human Brain Malformations and Teir Lessons for Neuronal Migration; Annu. Rev. Neurosci. 2001. 24:1041-70.

Christopher P. Austin, Lei Ma, Betty Ky, Jill A. Morris and Paul J. Sughrue; DISC1 (Disrupted in Schizophrenia-1) is expressed in limbic regions of the primate brain; Clinical Neuroscience and Neuropathology, vol. 14, No. 7, May 23, 2003, pp. 951-954.

Shinji Sasaki, Aki Shionoya, Michiyo Ishida, Michael J. Gambello, Jessica Yingling, Anthony Wynshaw-Boris, and Shinji Hirotsune; A LIS1/NUDEL/Cytoplasmic Dynein Heavy Chain Complex in the Developing and Adult Nervous System; Neuron, vol. 28, 681-696, Dec. 2000.

Akira Sawa, Fumitaka Oyama, Nigel J. Cairns, Naoji Amano, Masaaki Matsushita; Aberrant expression of bcl-2 gene family in Down's syndrome brains, Molecular Brain Research 48 (1997) 53-59.

Akira Sawa and Solomon H. Synder; Schizophrenia: diverse Approaches to a Complex disease; American Association for the Advancement of Science, Apr. 26, 2002, vol. 296, pp. 692-695.

Akira Sawa, Adil A. Khann, Lynda D. Hester, and Solomon H. Snyder; Glyceraldehyde-3-phosphate dehydrogenase: Nuclear translocation participates in neuronal and nonneuronal cell death; Proc. Natl. Acad. Sci. USA, vol. 94, pp. 11669-11674, Oct. 1997.

Akira Sawa, Gordon W. Wiegand, Jillian Cooper, Russell L. Margolis, Alan H. Sharp, Joseph F. Lawler Jr., J. Timothy Greenamyre, Solomon H. Snyder & Christopher A. Ross; Increased apoptosis of Huntington disease lymphoblasts associated withrepeat length-dependent mitochondrial depolarization; Nature Medicine, vol. 5, No. 10, Oct. 1999.

Naoya Sawamura, Jian-Sheng Gong, Wiliam S. Garver, Randall A. Heidenreich, Haruaki Ninomiya, Kousaku Ohno, Katsuhiko Yanagisawa, and Makoto Michikawa; Site-specific Phosphorylation of Tau Accompanied by Activation of Mitogen-activated Protein Kinase (MAPK) in Brains of Niemann-Pick Type C Mice; The Journal of Biological Chemistry; vol. 276, No. 13, Issue of Mar. 30, pp. 10314-10319, 2001.

Naoya Sawamura, Miheeko, Wenxin Ye, Kun Zou, Kentaro Hanada, Toshiharu Suzuki, Jian-Sheng Gong, Katsuhiro Yanagisawa, and Makoto Michikawa; Modulation of Amy lid Precursor Protein Cleavage by Cellular Sphingolipids; The Journal of Biological Chemistry, vol. 279, No. 12, Issue of Mar. 19, pp. 11984-11991, 2004.

IL Schurov, EJ Handford, NJ Brandon and PJ Whiting; Expression of disrupted in schizophrenia (DISC1) protein in the adult and developing mouse brain indicates its role in neurodevelopment; Molecular Psychiatry (2004) 9, 1100-1110.

Lynn D. Selemon and Patricia S. Goldman-Rakic; The Reduced Neuropil Hypothesis: a Circuit Based Model of Schizophrenia; 1999 Society of Biological Psychiatry, 1999, 45:17-25.

Deanna S. Smith, Martin Niethammer, Ramses Ayala, Yin Zhou, Michael J. Gambello, Anthony Wynshaw-Boris, and Li-Huei Tsai; Regulation of cytoplasmic dynein behaviour and microtubule organization by mammalian Lis1; Nature Cell Biology, vol. 2, Nov. 2000, pp. 767-775.

Antoine Bechara, Hanna Damasio and Antonio R. Damasio; Emotion, Decision Making and the Orbitofrontal Cortex; Cerebral Cortex Mar. 2000; 10:295-307;1047-3211/00.

David StClair, Douglas Blackwood, Walter Muir, Andrew Carothers, Maura Walker, Geroge Spowart, Christine Gosden, and H. John Evans; Association within a family of a balanced autosomal translocation with major mental illness; The Lancet, vol. 336, pp. 13-16, Jul. 7, 1990.

Shinji Sudoh, Yuuki Kawammura, Shinji Sato, Rong Wang, Takaomi C. Saido, Fumitaka Oyama, Yoshiyuki Sakaki, Hiroto Komano, and Katushiko Yanagisawa; *Presnilin 1* Mutations Linked to Familial Alzheimer's Disease Increase the Intracellular Levels of Amyloid β-Protein 1-42 and Its N-Terminally Truncated Variant(s) Which Are Generated at Distinct Sites; Journal of Neurochemistry, vol. 71, No. 4, 1998, pp. 1535-1543.

H. Tabata and K. Nakajima; Efficient In Utero Gene Transfer System to the Developing Mouse Brain Using Electroporation: Visualization of Neuronal Migration in the Developing Cortex; Neuroscience, vol. 103, No. 4, pp. 865-872, 2001.

Martin S. Taylor, Rebecca S. Devon, J. Kirsty Millar, and David Porteous; Evolutionary constraints on the Disrupted in Schizophrenia locus; Science Direct, Genomics, 81 (2003) 67-77.

Dmitri Tkachev, Michael L. Mimmack, Margaret M Ryan, Matt Wayland, Tom Freeman, Peter B Jones, Michael Starkey, Mare J Webster, Robert H. Yolken, Sabine Bahn; Oligodendrocyte dysfunction in schizophrenia and bipolar disorder; The Lancet, vol. 362, Sep. 6, 2003, pp. 798-805.

Toshifumi Tomoda, Jee Hae Kim, Caixin Zhan, and Mary E. Hatten; Role of Unc51.1 and its binding partners in CNS axon outgrowth; Genes & Development 18:541-558, 2004.

E. Fuller Torrey; Epidemiological comparison of schizophrenia and bipolar disorder; Elsevier, Schizophrenia Research 39 (1999) 101-106.

E. Fuller Torrey, Maree Webster, Mihcael Knable, Nancy Johnston, Robert H. Yolken; The Stanley Foundation brain collection and Neuropathology Consortium; Elsevier, Schizophrenia Research 44 (2000) 151-155.

Nora d. Volkow and Joanna S. Fowler; Addiction, a Disease of Complusion and Drive: Involvement in the Orbitofrontal Cortex; Cerebral Cortex, Mar. 2000, 10:318-325;1047-3211.

Clare M. Waterman-Storer, Sher B. Karki, Sergei A. Kuznetsov, Joel S. Tabb, Dieter G. Weiss, George M. Langford, and Erika L.F. Holzbaur; The interaction between cytoplasmic dynein and dyactin is required for fast axonal transport; Proc. Natl. Acad. Sci., USA, vol. 94, pp. 12180-12185, Oct. 1997.

Wade H. Berrettini; Are Schizophrenic and Bipolar disorders *Related?* A Review of Family and Molecular Studies; 2000 society of Biological Psychiatry, pp. 531-538.

Daniel R. Weinberger, MD., Implications of Normal Brain Development for the Pathogenesis of Schizophrenia; Arch Gen Psychiatry vol. 44, Jul. 1987, pp. 660-669.

Zhigang Xie, Kamon Sanada, Benjamin Adam Smauels, Heather Shih, and Li-Huei Tsai; Serine 732 Phosphorylation of FAK by Cdk5 Is Important for Microtubule Organization, Nuclear Movement, and Neuronal Migration; Cell Press, vol. 114, 469-482, Aug. 22, 2003.

Jenn-Yah Yu, Stacy L. Deruiter, and David L. Turner; RNA interference by expression of short-interfering RNAs and hairpin RNAs in mammalian cells; PNAS/ Apr. 30, 2002, vol. 99, No. 9, 6047-6052.

Wade H. Berrettini; Susceptibility Loci for Bipolar disorder: Overlap with Inherited Vulnerability to Schizophrenia; 2000 Society of Biological Psychiatry, pp. 245-251.

\* cited by examiner

Figure 2
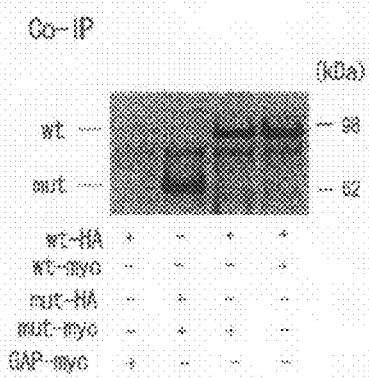
Fig. 2A
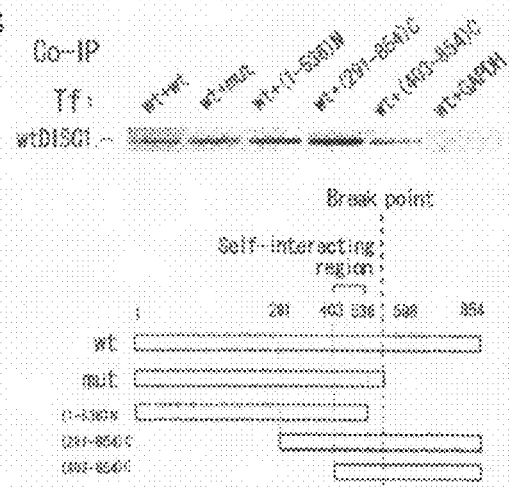
Fig. 2B
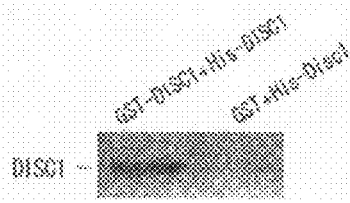
Fig. 2C In vitro binding
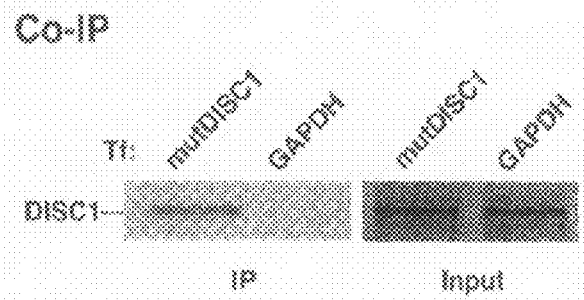
Fig. 2D

Figure 3
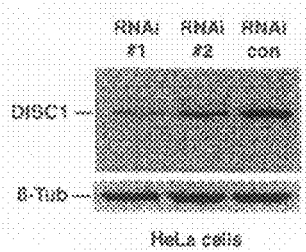
Fig. 3A
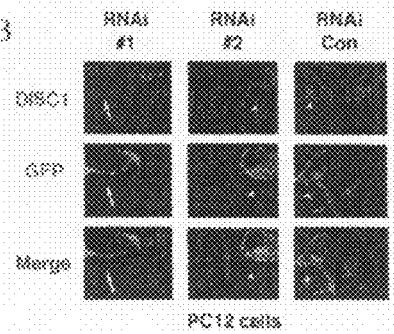
Fig. 3B
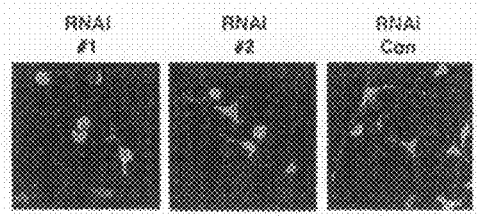
Fig. 3C
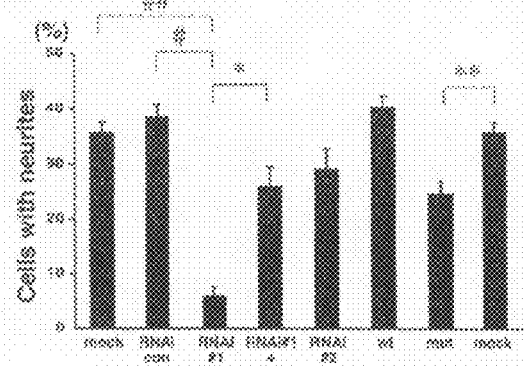
Fig. 3D

Figure 5
Fig. 5A
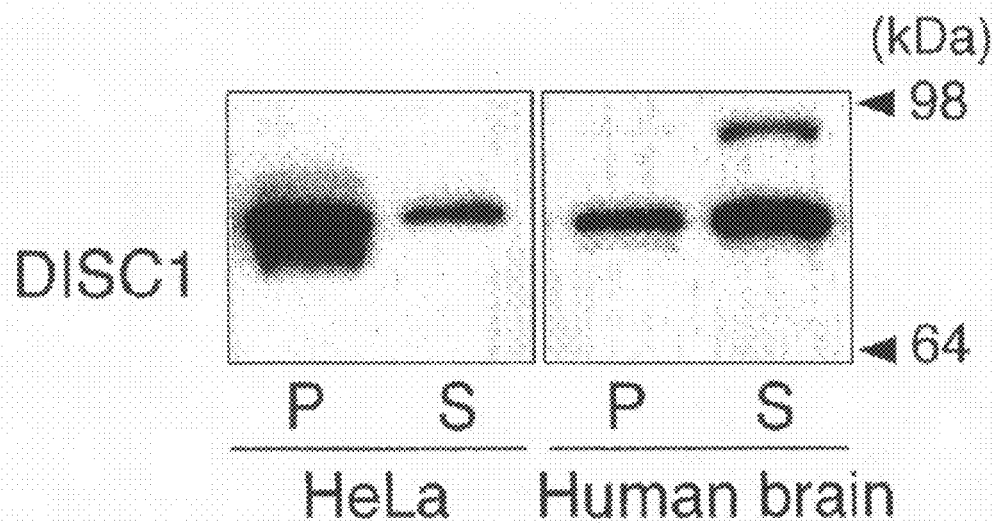
Fig. 5B
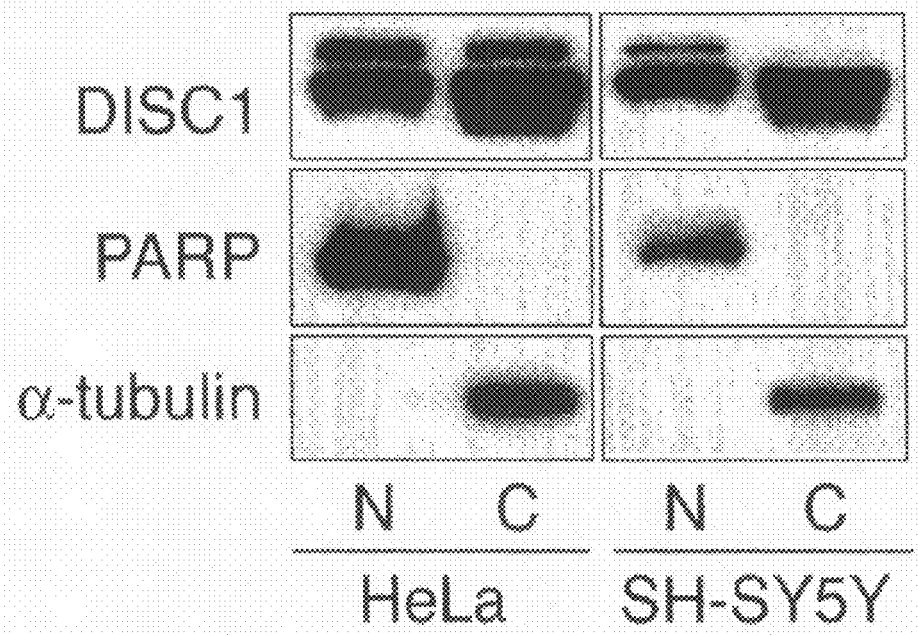

Figure 7
Fig. 7A
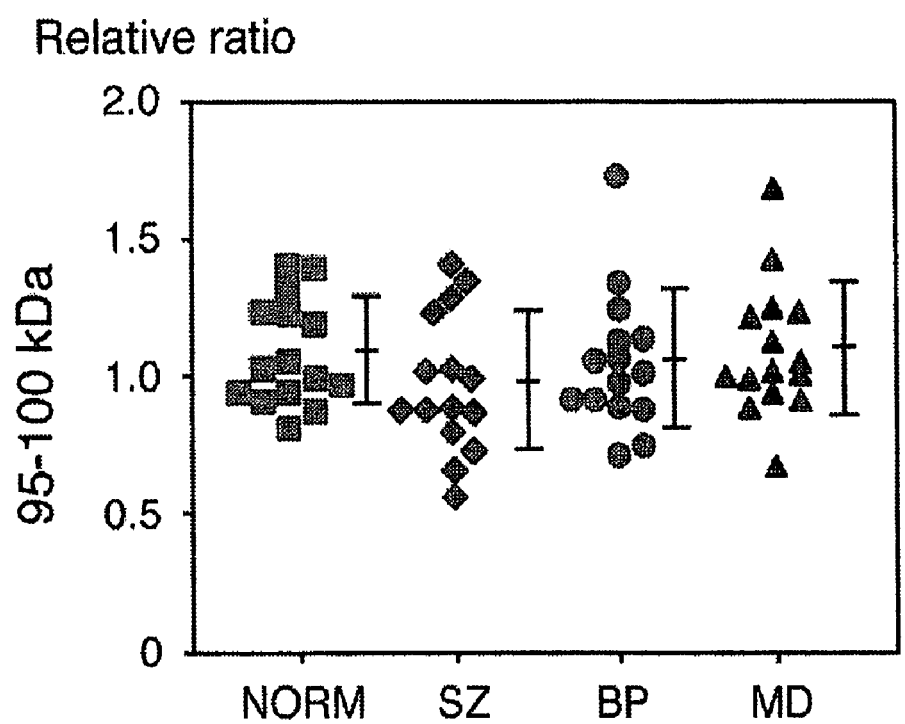
Fig. 7B
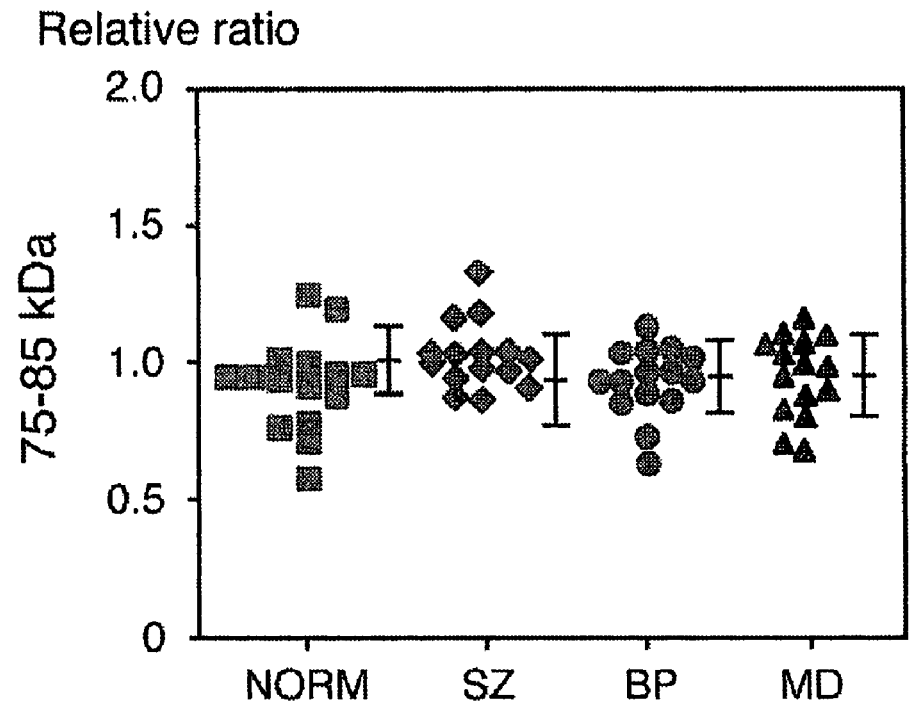

Fig. 11A    RT-PCR

HeLa  LB          HeLa  LB
Exons 4-5         Exons 8-9

Fig. 11B    Western blotting

Figure 12
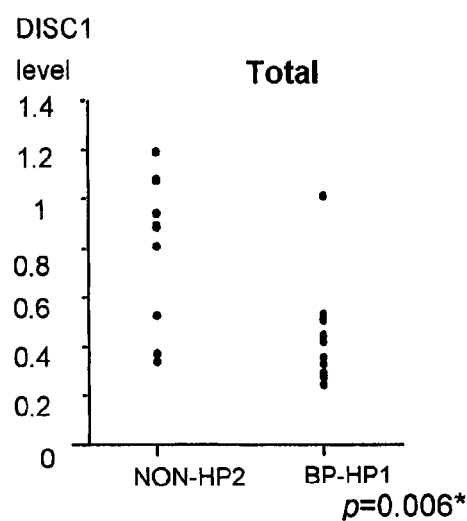
Fig. 12A
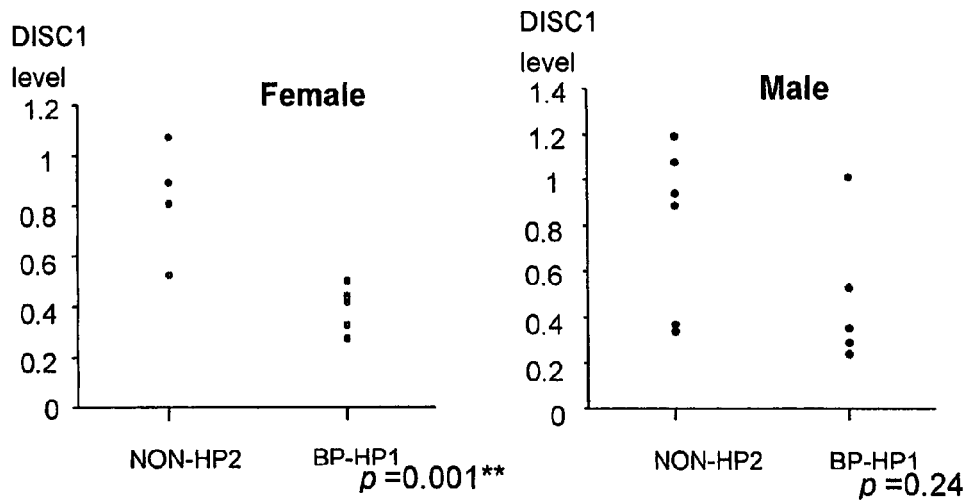
Fig. 12B
Fig. 12C
|  | DISC1 Expression | | | | |
|---|---|---|---|---|---|
|  |  | | BP-HP1 | | |
|  | Mean | SD | Mean | SD | p value |
| All | 0.77 | 0.31 | 0.44 | 0.20 | 0.006* |
| Female | 0.83 | 0.23 | 0.41 | 0.08 | 0.001** |
| Male | 0.74 | 0.37 | 0.49 | 0.31 | 0.240 |

Antibody against human and rodent DISC1

SEQUENCE LISTING

```
<160> NUMBER OF SEQ ID NOS: 65

<210> SEQ ID NO 1
<211> LENGTH: 19
<212> TYPE: DNA
<213> ORGANISM: Artificial Sequence
<220> FEATURE:
<223> OTHER INFORMATION: RNA interference inducing sequence

<400> SEQUENCE: 1
ggcaaacact gtgaagtgc                                                  19

<210> SEQ ID NO 2
<211> LENGTH: 19
<212> TYPE: DNA
<213> ORGANISM: Artificial Sequence
<220> FEATURE:
<223> OTHER INFORMATION: RNA interference inducing sequence

<400> SEQUENCE: 2
cggctgagcc aagagttgg                                                  19
```

<210> SEQ ID NO 3
<211> LENGTH: 21
<212> TYPE: DNA
<213> ORGANISM: Artificial Sequence
<220> FEATURE:
<223> OTHER INFORMATION: Forward primer

<400> SEQUENCE: 3
gactcgctga ggagaagaaa g                                                    21

<210> SEQ ID NO 4
<211> LENGTH: 20
<212> TYPE: DNA
<213> ORGANISM: Artificial Sequence
<220> FEATURE:
<223> OTHER INFORMATION: Reverse primer

<400> SEQUENCE: 4
ggttgttaac agaggcacgc                                                      20

<210> SEQ ID NO 5
<211> LENGTH: 21
<212> TYPE: DNA
<213> ORGANISM: Artificial Sequence
<220> FEATURE:
<223> OTHER INFORMATION: Forward primer

<400> SEQUENCE: 5
ttctccagat gcagttccag c                                                    21

<210> SEQ ID NO 6
<211> LENGTH: 21
<212> TYPE: DNA
<213> ORGANISM: Artificial Sequence
<220> FEATURE:
<223> OTHER INFORMATION: Reverse primer

<400> SEQUENCE: 6
tatccatggc tgcaaactct t                                                    21

<210> SEQ ID NO 7
<211> LENGTH: 22
<212> TYPE: DNA
<213> ORGANISM: Artificial Sequence
<220> FEATURE:
<223> OTHER INFORMATION: Forward primer

<400> SEQUENCE: 7
cagcccctac tgtgacctct gt                                                   22

<210> SEQ ID NO 8
<211> LENGTH: 23
<212> TYPE: DNA
<213> ORGANISM: Artificial Sequence
<220> FEATURE:
<223> OTHER INFORMATION: Reverse primer

<400> SEQUENCE: 8
aagactgaag ggccgagaga gac                                                  23

<210> SEQ ID NO 9
<211> LENGTH: 20
<212> TYPE: DNA
<213> ORGANISM: Artificial Sequence
<220> FEATURE:
<223> OTHER INFORMATION: Forward primer

<400> SEQUENCE: 9
gaacgtggag aagcagaagg                                                    20

<210> SEQ ID NO 10
<211> LENGTH: 20
<212> TYPE: DNA
<213> ORGANISM: Artificial Sequence
<220> FEATURE:
<223> OTHER INFORMATION: Reverse primer

<400> SEQUENCE: 10
ggaagtcagt tgagcccaga                                                    20

<210> SEQ ID NO 11
<211> LENGTH: 23
<212> TYPE: DNA
<213> ORGANISM: Artificial Sequence
<220> FEATURE:
<223> OTHER INFORMATION: Forward primer

<400> SEQUENCE: 11
gaaactaatg catctggcat tga                                                23

<210> SEQ ID NO 12
<211> LENGTH: 22
<212> TYPE: DNA
<213> ORGANISM: Artificial Sequence
<220> FEATURE:
<223> OTHER INFORMATION: Reverse primer

<400> SEQUENCE: 12
tgggacatga tgacaaaaca at                                                 22

<210> SEQ ID NO 13
<211> LENGTH: 23
<212> TYPE: DNA
<213> ORGANISM: Artificial Sequence
<220> FEATURE:
<223> OTHER INFORMATION: Forward primer

<400> SEQUENCE: 13 caccgggggtt atctattttg cat                                               23

<210> SEQ ID NO 14
<211> LENGTH: 22
<212> TYPE: DNA
<213> ORGANISM: Artificial Sequence
<220> FEATURE:
<223> OTHER INFORMATION: Reverse primer

<400> SEQUENCE: 14 tgagggaaa atggtgacaa ta                                                  22

<210> SEQ ID NO 15
<211> LENGTH: 21
<212> TYPE: DNA
<213> ORGANISM: Artificial Sequence
<220> FEATURE:
<223> OTHER INFORMATION: Forward primer

<400> SEQUENCE: 15
catgaggatt tcagcttctg c                                                  21

<210> SEQ ID NO 16

```
<211> LENGTH: 21
<212> TYPE: DNA
<213> ORGANISM: Artificial Sequence
<220> FEATURE:
<223> OTHER INFORMATION: Reverse primer

<400> SEQUENCE: 16
gcaagaccct gtctcaaaga a                                              21

<210> SEQ ID NO 17
<211> LENGTH: 20
<212> TYPE: DNA
<213> ORGANISM: Artificial Sequence
<220> FEATURE:
<223> OTHER INFORMATION: Forward primer

<400> SEQUENCE: 17
ggtgcatatg gccaattctc                                                20

<210> SEQ ID NO 18
<211> LENGTH: 21
<212> TYPE: DNA
<213> ORGANISM: Artificial Sequence
<220> FEATURE:
<223> OTHER INFORMATION: Reverse primer

<400> SEQUENCE: 18
ccaatgaaca ggtcaaagag g                                              21

<210> SEQ ID NO 19
<211> LENGTH: 21
<212> TYPE: DNA
<213> ORGANISM: Artificial Sequence
<220> FEATURE:
<223> OTHER INFORMATION: Forward primer

<400> SEQUENCE: 19
gtggaaggtt cacttttgc a                                               21

<210> SEQ ID NO 20
<211> LENGTH: 22
<212> TYPE: DNA
<213> ORGANISM: Artificial Sequence
<220> FEATURE:
<223> OTHER INFORMATION: Reverse primer

<400> SEQUENCE: 20
tgcagaagcc aggtatccta ag                                             22

<210> SEQ ID NO 21
<211> LENGTH: 21
<212> TYPE: DNA
<213> ORGANISM: Artificial Sequence
<220> FEATURE:
<223> OTHER INFORMATION: Forward primer

<400> SEQUENCE: 21
aatctctgac ctggctgttc c                                              21

<210> SEQ ID NO 22
<211> LENGTH: 22
<212> TYPE: DNA
<213> ORGANISM: Artificial Sequence
<220> FEATURE:
<223> OTHER INFORMATION: Reverse primer

<400> SEQUENCE: 22
```

```
acgatgtgct ggtagctgtc at                                              22

<210> SEQ ID NO 23
<211> LENGTH: 22
<212> TYPE: DNA
<213> ORGANISM: Artificial Sequence
<220> FEATURE:
<223> OTHER INFORMATION: Forward primer

<400> SEQUENCE: 23
tcttccatgt gtgtggatgc tg                                              22

<210> SEQ ID NO 24
<211> LENGTH: 20
<212> TYPE: DNA
<213> ORGANISM: Artificial Sequence
<220> FEATURE:
<223> OTHER INFORMATION: Reverse primer

<400> SEQUENCE: 24
actttgccgg ggaacagttg                                                 20

<210> SEQ ID NO 25
<211> LENGTH: 22
<212> TYPE: DNA
<213> ORGANISM: Artificial Sequence
<220> FEATURE:
<223> OTHER INFORMATION: Forward primer

<400> SEQUENCE: 25
tcaatccttt ggctttgagc tt                                              22

<210> SEQ ID NO 26
<211> LENGTH: 20
<212> TYPE: DNA
<213> ORGANISM: Artificial Sequence
<220> FEATURE:
<223> OTHER INFORMATION: Reverse primer

<400> SEQUENCE: 26
ctggccagcc tttttcatcg                                                 20

<210> SEQ ID NO 27
<211> LENGTH: 21
<212> TYPE: DNA
<213> ORGANISM: Artificial Sequence
<220> FEATURE:
<223> OTHER INFORMATION: Forward primer

<400> SEQUENCE: 27
agccaggtag acaagctatc g                                               21

<210> SEQ ID NO 28
<211> LENGTH: 21
<212> TYPE: DNA
<213> ORGANISM: Artificial Sequence
<220> FEATURE:
<223> OTHER INFORMATION: Reverse primer

<400> SEQUENCE: 28
gaataagggt cccctctgga g                                               21

<210> SEQ ID NO 29
<211> LENGTH: 22
<212> TYPE: DNA
```

```
<213> ORGANISM: Artificial Sequence
<220> FEATURE:
<223> OTHER INFORMATION: Forward primer

<400> SEQUENCE: 29
gtccacggca ctaacaagtg at                                              22

<210> SEQ ID NO 30
<211> LENGTH: 23
<212> TYPE: DNA
<213> ORGANISM: Artificial Sequence
<220> FEATURE:
<223> OTHER INFORMATION: Reverse primer

<400> SEQUENCE: 30
ccatcttctg aggcatgaaa aac                                             23

<210> SEQ ID NO 31
<211> LENGTH: 20
<212> TYPE: DNA
<213> ORGANISM: Artificial Sequence
<220> FEATURE:
<223> OTHER INFORMATION: Forward primer

<400> SEQUENCE: 31
agagggccac gatcaccttc                                                 20

<210> SEQ ID NO 32
<211> LENGTH: 22
<212> TYPE: DNA
<213> ORGANISM: Artificial Sequence
<220> FEATURE:
<223> OTHER INFORMATION: Reverse primer

<400> SEQUENCE: 32
atctccgtaa ttgattcagg ca                                              22

<210> SEQ ID NO 33
<211> LENGTH: 16
<212> TYPE: DNA
<213> ORGANISM: Artificial Sequence
<220> FEATURE:
<223> OTHER INFORMATION: Forward primer

<400> SEQUENCE: 33
acgaggaccc gcgatg                                                     16

<210> SEQ ID NO 34
<211> LENGTH: 20
<212> TYPE: DNA
<213> ORGANISM: Artificial Sequence
<220> FEATURE:
<223> OTHER INFORMATION: Reverse primer

<400> SEQUENCE: 34
acccgtgtag ccaagagact                                                 20

<210> SEQ ID NO 35
<211> LENGTH: 16
<212> TYPE: DNA
<213> ORGANISM: Artificial Sequence
<220> FEATURE:
<223> OTHER INFORMATION: Probe

<400> SEQUENCE: 35
tctctctcag cccttc                                                     16
```

<210> SEQ ID NO 36
<211> LENGTH: 14
<212> TYPE: DNA
<213> ORGANISM: Artificial Sequence
<220> FEATURE:
<223> OTHER INFORMATION: Probe

<400> SEQUENCE: 36
tctctcggcc cttc                                                      14

<210> SEQ ID NO 37
<211> LENGTH: 17
<212> TYPE: DNA
<213> ORGANISM: Artificial Sequence
<220> FEATURE:
<223> OTHER INFORMATION: Forward primer

<400> SEQUENCE: 37
caggccgcaa ggaacag                                                   17

<210> SEQ ID NO 38
<211> LENGTH: 24
<212> TYPE: DNA
<213> ORGANISM: Artificial Sequence
<220> FEATURE:
<223> OTHER INFORMATION: Reverse primer

<400> SEQUENCE: 38
ggtccatgtc tggtaaagaa tgca                                           24

<210> SEQ ID NO 39
<211> LENGTH: 14
<212> TYPE: DNA
<213> ORGANISM: Artificial Sequence
<220> FEATURE:
<223> OTHER INFORMATION: Probe

<400> SEQUENCE: 39
acgctctggc ctgg                                                      14

<210> SEQ ID NO 40
<211> LENGTH: 15
<212> TYPE: DNA
<213> ORGANISM: Artificial Sequence
<220> FEATURE:
<223> OTHER INFORMATION: Probe

<400> SEQUENCE: 40
cacgctctag cctgg                                                     15

<210> SEQ ID NO 41
<211> LENGTH: 28
<212> TYPE: DNA
<213> ORGANISM: Artificial Sequence
<220> FEATURE:
<223> OTHER INFORMATION: Forward primer

<400> SEQUENCE: 41
ccctcaactt gtcacttaaa gaaatcac                                       28

<210> SEQ ID NO 42
<211> LENGTH: 27
<212> TYPE: DNA
<213> ORGANISM: Artificial Sequence
<220> FEATURE:

-continued

```
<223> OTHER INFORMATION: Reverse primer

<400> SEQUENCE: 42
agtcaaacga aaacttcata ggcttct                                        27

<210> SEQ ID NO 43
<211> LENGTH: 24
<212> TYPE: DNA
<213> ORGANISM: Artificial Sequence
<220> FEATURE:
<223> OTHER INFORMATION: Probe

<400> SEQUENCE: 43
aaaatgggaa tataaaggta ctta                                           24

<210> SEQ ID NO 44
<211> LENGTH: 22
<212> TYPE: DNA
<213> ORGANISM: Artificial Sequence
<220> FEATURE:
<223> OTHER INFORMATION: Probe

<400> SEQUENCE: 44
aatgggaata taaaggtgct ta                                             22

<210> SEQ ID NO 45
<211> LENGTH: 23
<212> TYPE: DNA
<213> ORGANISM: Artificial Sequence
<220> FEATURE:
<223> OTHER INFORMATION: Forward primer

<400> SEQUENCE: 45
caacgtgctg taggaaacca ttt                                            23

<210> SEQ ID NO 46
<211> LENGTH: 25
<212> TYPE: DNA
<213> ORGANISM: Artificial Sequence
<220> FEATURE:
<223> OTHER INFORMATION: Reverse primer

<400> SEQUENCE: 46
cagcccttct ctctctgatg ttaat                                          25

<210> SEQ ID NO 47
<211> LENGTH: 16
<212> TYPE: DNA
<213> ORGANISM: Artificial Sequence
<220> FEATURE:
<223> OTHER INFORMATION: Probe

<400> SEQUENCE: 47
ctcggtgagg tcttta                                                    16

<210> SEQ ID NO 48
<211> LENGTH: 15
<212> TYPE: DNA
<213> ORGANISM: Artificial Sequence
<220> FEATURE:
<223> OTHER INFORMATION: Probe

<400> SEQUENCE: 48
tcggtgaagt cttta                                                     15
```

<210> SEQ ID NO 49
<211> LENGTH: 22
<212> TYPE: DNA
<213> ORGANISM: Artificial Sequence
<220> FEATURE:
<223> OTHER INFORMATION: Forward primer

<400> SEQUENCE: 49
gacttggaag cttgtcgatt gc                                              22

<210> SEQ ID NO 50
<211> LENGTH: 17
<212> TYPE: DNA
<213> ORGANISM: Artificial Sequence
<220> FEATURE:
<223> OTHER INFORMATION: Reverse primer

<400> SEQUENCE: 50
gcttcccctg gcttcct                                                    17

<210> SEQ ID NO 51
<211> LENGTH: 17
<212> TYPE: DNA
<213> ORGANISM: Artificial Sequence
<220> FEATURE:
<223> OTHER INFORMATION: Probe

<400> SEQUENCE: 51
ctgtaggcac tggataa                                                    17

<210> SEQ ID NO 52
<211> LENGTH: 17
<212> TYPE: DNA
<213> ORGANISM: Artificial Sequence
<220> FEATURE:
<223> OTHER INFORMATION: Probe

<400> SEQUENCE: 52
ctgtaggctc tggataa                                                    17

<210> SEQ ID NO 53
<211> LENGTH: 28
<212> TYPE: DNA
<213> ORGANISM: Artificial Sequence
<220> FEATURE:
<223> OTHER INFORMATION: Forward primer

<400> SEQUENCE: 53
tgctgaattt ccttctaaat gtcactca                                        28

<210> SEQ ID NO 54
<211> LENGTH: 26
<212> TYPE: DNA
<213> ORGANISM: Artificial Sequence
<220> FEATURE:
<223> OTHER INFORMATION: Reverse primer

<400> SEQUENCE: 54
aattcacccc aacttctctc taatgg                                          26

<210> SEQ ID NO 55
<211> LENGTH: 15
<212> TYPE: DNA
<213> ORGANISM: Artificial Sequence
<220> FEATURE:
<223> OTHER INFORMATION: Probe

```
<400> SEQUENCE: 55
attcttggga atgtc                                                          15

<210> SEQ ID NO 56
<211> LENGTH: 16
<212> TYPE: DNA
<213> ORGANISM: Artificial Sequence
<220> FEATURE:
<223> OTHER INFORMATION: Probe

<400> SEQUENCE: 56
cattcttgag aatgtc                                                         16

<210> SEQ ID NO 57
<211> LENGTH: 32
<212> TYPE: DNA
<213> ORGANISM: Artificial Sequence
<220> FEATURE:
<223> OTHER INFORMATION: Forward primer

<400> SEQUENCE: 57
acgcgtcgac ccagccagct cttagcagtt tc                                       32

<210> SEQ ID NO 58
<211> LENGTH: 21
<212> TYPE: DNA
<213> ORGANISM: Artificial Sequence
<220> FEATURE:
<223> OTHER INFORMATION: Reverse primer

<400> SEQUENCE: 58
aacagcctcg gctccattct c                                                   21

<210> SEQ ID NO 59
<211> LENGTH: 20
<212> TYPE: DNA
<213> ORGANISM: Artificial Sequence
<220> FEATURE:
<223> OTHER INFORMATION: Forward primer

<400> SEQUENCE: 59
gcaccctgag gaagaaagtt                                                     20

<210> SEQ ID NO 60
<211> LENGTH: 24
<212> TYPE: DNA
<213> ORGANISM: Artificial Sequence
<220> FEATURE:
<223> OTHER INFORMATION: Reverse primer

<400> SEQUENCE: 60
tctcttctca gtctgttgta atct                                                24

<210> SEQ ID NO 61
<211> LENGTH: 7
<212> TYPE: PRT
<213> ORGANISM: Homo sapiens

<400> SEQUENCE: 61

Gln Cys Gly Leu Asp Ser Arg
1               5

<210> SEQ ID NO 62
<211> LENGTH: 11
<212> TYPE: PRT
```

```
-continued

<213> ORGANISM: Homo sapiens

<400> SEQUENCE: 62

Ser Ala Ala Ala Pro Thr Val Thr Ser Val Arg
1               5                   10

<210> SEQ ID NO 63
<211> LENGTH: 8
<212> TYPE: PRT
<213> ORGANISM: Homo sapiens

<400> SEQUENCE: 63

Gly Gly Thr Arg Leu Pro Asp Arg
1               5

<210> SEQ ID NO 64
<211> LENGTH: 8
<212> TYPE: PRT
<213> ORGANISM: Homo sapiens

<400> SEQUENCE: 64

Arg Asp Trp Leu Leu Gln Glu Lys
1               5

<210> SEQ ID NO 65
<211> LENGTH: 5
<212> TYPE: PRT
<213> ORGANISM: Homo sapiens

<400> SEQUENCE: 65

Gln Gln Leu Gln Lys
1               5
```

METHOD FOR DIAGNOSING OR PREDICTING SUSCEPTIBILITY TO PSYCHIATRIC DISORDERS

CROSS-REFERENCE TO RELATED APPLICATION

This application claims the benefit of a previously filed Provisional Application No. 60/539,900 filed Jan. 28, 2004, the whole contents of which is hereby incorporated by reference.

BACKGROUND OF THE INVENTION

1. Technical Field

The present invention relates to a method for diagnosing or predicting susceptibility to a psychiatric disorder, especially schizophrenia, bipolar disorder and the like.

2. Art Related

Currently differential diagnosis for psychiatric disorders is largely phenomenological. Diagnosis is based on observation of certain subset of symptoms and the course of disorders. The Diagnostic and Statistical Manual (DSM) of Mental Disorders (the American Psychiatric Association's Diagnostic and Statistical Manual of Mental Disorders, 4$^{th}$ edition, 1994) is widely used. Although considerable research efforts have been conducted for developing biological and biochemical assessment to psychiatric disorders, almost none of objective markers has been utilized in their diagnostic criteria.

Schizophrenia is one of the most devastating psychiatric disorders, as defined by DSM-IV, characterized by psychotic symptoms involving disturbances of thought, emotion, and perception.

Schizophrenia occurs worldwide as a common disease such as hypertension and diabetic etc. Although its etiology remains elusive, multiple lines of evidence favor genetic predisposition to schizophrenia. Linkage analyses for schizophrenia have indicated multiple chromosomal loci, suggesting the existence of certain candidate genes as its susceptibility factors. Brain imaging and neuropathological assessments suggest that abnormalities in schizophrenic include aberrant cerebral cortical development that might reflect cytoskeletal disturbances.

In a Scottish family, a balanced chromosome (1;11)(q42.1; q14.3) translocation associates with occurrence of major psychiatric disorders (schizophrenia and mood disorders) with a logarithm of odds score of 7.1. This translocation interrupts the coding sequences of a transcript, named as Disrupted-in Schizophrenia-1 (DISC1), leading to loss of the C-terminal 257 amino acids for DISC1 protein.

It was reported that transient expression of mutant DISC1 protein (mutDISC1), but not wild-type DISC1 protein (wtDISC1) in PC12 cells inhibits neurite outgrowth (PNAS vol. 100, No. 1, 289-294, 2003). It has also been reported that stable transfection of wtDISC1 in PC12 cells enhances neurite extension (Molecular Psychiatry vol. 8, No. 7, 685-694, 2003).

wtDISC1 is expressed mainly in the centrosome, in contrast, mutDISC1 widely distributed in the cytoplasm (PNAS vol. 100, No. 1, 289-294, 2003, Human Molecular Genetics vol. 12, No. 13, 1591-1608, 2003).

Although these prior arts have provided information on subcellular localization of DISC1 and clues for its functions, they have not addressed pathophysiology when wtDISC1 is impaired. Thus, involvement of DISC1 in more general schizophrenia and related mental illnesses, without the unique mutation of DISC1 (mutDISC1) found in the Scottish family, is still unclear.

SUMMARY OF THE INVENTION

In the present specification and claims, "psychiatric disorders" may include, but not limited to, schizophrenia, mood disorder such as bipolar disorder, substance abuse.

The present invention provides a method for diagnosing or predicting susceptibility to a psychiatric disorder in an individual, which comprises confirming subcellular distribution and/or molecular diversity of DISC 1 in the cells from the individual.

According to the present invention, subcellular distribution of DISC1 may be determined by any of known method including subcellular fraction of the cells and evaluating quantitatively or semi-quantitatively the fractions, or visualizing the protein in the cell. It will be convenient to evaluate subcellular distribution of DISC1 or its isoform by its nuclear to cytplasmic ratio or crude nuclear pellet (P) to postnuclear supernatant (S) ratio.

According to the present specification and claims, the term "molecular diversity" may include expression level of DISC1 at both mRNA and protein levels, the amount of impairment of DISC1 at the expression levels and/or functions. Molecular diversity may be linked to a variety of haplotypes. Therefore, "a confirmation of molecular diversity of DISC1" implies confirmation of alteration in DISC1 at the expression levels and/or functions. The examples of possible mechanisms for the alteraion include deficits in transactivation of DISC1 gene, abnormalities in splicing (exon usage), changes in RNA stability, and point mutations of DISC1 protein.

According to the present invention, subcellular distribution and/or molecular diversity of DISC1 may be determined by using antibody to DISC1. Antibodies may be monoclonal or polyclonal. An example of antibodies to various epitopes on DISC1 are shown in FIG. 13. A kit with the antibodies for conducting the method of the present invention can be provided. One embodiment is that the antibodies in the kit are conjugated to reagents including a secondary antibody and a detectable marker.

The specimens from the individual and control subjects to be tested based on the invention may be bloods, fibroblasts, mucous membranes, olfactory epitheliums and lymphoblasts.

To date, human fibroblast, olfactory epithelium cells and lymphoblasts are becoming an increasingly popular cellular system for study of gene expression or other cellular functions. The advantage is the ready accessibility of the tissue compared to neural tissue. (Arnold S E et al. 2001; Feron F et al 1999; Moberg P J, et al. 1999; Taylor, M. S. et al. 2003; Farbman A I. 1994; Crews L et al 1994; Panov A V et al 2002)

In one embodiment, diagnosing or predicting susceptibility to bipolar disorder can be conducted by measuring expression level of DISC1 in lymphoblasts of the individual.

According to another aspect of the present invention, a novel risk haplotype DISC-1 for psychiatric disorder is provided. The risk haplotype consists of the combination of SNPs shown below:

| | SNP ID | Location | | base |
|---|---|---|---|---|
| 1 | rs1538975 | 228,863,377 | intron 1/2 | G |
| 2 | rs3738401 | 228,865,300 | Exon 2 | G |

-continued

| | SNP ID | Location | | base |
|---|---|---|---|---|
| 3 | Novel SNP | 228,865,369 | Exon 2 | C |
| 4 | rs1954175 | 228,890,415 | intron 3/4 | A |
| 5 | rs2273890 | 228,966,053 | intron 7/8 | T |
| 6 | rs1407598 | 228,981,830 | intron 8/9 | A |
| 7 | rs6675281 | 228,989,104 | Exon 9 | C |
| 8 | rs1000731 | 228,998,496 | intron 9/10 | G |
| 9 | rs821653 | 229,161,892 | intron 10/11 | T |
| 10 | rs821616 | 229,179,608 | Exon 11 | A |
| 11 | rs3524 | 229,193,684 | intron 11/12 | C |
| 12 | rs3737597 | 229,207,839 | Exon 13 | G |

Where the physical location is based on build 34 of NCBI. db SNP is availale from the website named ncbi.nlm.nih.gov/SNP/.

In the present specification, the risk haplotype is denoted as HP1. The haplotype HP1 is over-transmitted to affected individuals with psychiatric disorder such as bipolar disorder, especially, in female patients.

Accordingly, the present invention further provides a method for diagnosing or predicting susceptibility to a psychiatric disorder in an individual, which comprises determining the presence or absence of the haplotype HP1 in the individual. It is well known to the art that the procedure to determine the presence or absence of a haplotype in the individual.

In further aspect of the present invention, confirming molecular diversity and/or subcellular distribution of DISC1 may be used for screening an agent for the treatment of psychiatric disorders.

BRIEF DESCRIPTION OF THE DRAWINGS

FIG. 1A wtDISC1 was distributed predominantly in the perinuclear regions of the COS-7 cells, especially in the centrosome. In contrast, mutDISC1 was distributed widely in the cytoplasm. A unique redistribution of wtDISC 1 from the discrete perinuclear regions to diffuse organization in the cytoplasm occurred when wtDISC 1 is co-expressed with mutDISC 1.

FIG. 1B Redistribution of wtDISC1 by co-expression of mutDISC1 was observed in a glycerol density gradient.

FIGS. 2A-2D Dominant-negative effects of mutDISC 1

FIG. 2A Co-immunoprecipitation of exogenous wtDISC1-HA/wtDISC1-myc, wtDISC1-HA/mutDISC1-myc, or mutDISC1-HA/mutDISC1-myc in HEK293 cells. Both wt and/or mutDISC1 self-associate. GAPDH-myc did not co-immunoprecipitate with wtDISC1-HA. An anti-myc antibody and -HA antibody were used for precipitation and Western blotting, respectively.

FIG. 2B Domain mapping for DISC1 self-association. A series of DISC1 mutants with HA- tag depicted in the lower panel were tested for co-immunoprecipitation with an anti-HA antibody. Immunoprecipitates were analyzed on SDS-PAGE, followed by Western blotting with an anti-myc antibody. The putative self-interacting region comprises amino acids 403-536 of DISC1.

FIG. 2C DISC 1 self-associates via direct protein-protein binding. GST- and His-tagged DISC 1 protein fragments (amino acids 347-600) co-precipitate with glutathione-beads.

FIG. 2D Co-immunoprecipitation of endogenous DISC 1 with HA-tagged mutDISC 1, but not HA-GAPDH, in differentiated PC12 cells. Immunoprecipitation with an anti-HA antibody was followed by analysis of the immunoprecipitates on SDS-PAGE and Western blotting with an antibody against the C-terminal domain of DISC1 (the domain deficient in mutDISC1)

FIGS. 3A-3D Requirement of DISC1 for neurite outgrowth in differentiating PC12 cells FIG. 3A Influence of shRNA (RNAi#1, #2) on DISC1 protein levels in HeLa cells was evaluated by Western blotting. RNAi#1 and #2 suppress 90% and 40% of DISC1 expression, respectively.

FIG. 3B Suppression of DISC1 by shRNA in PC12 cells. The representative images were depicted 3 days after transfection of RiNAi#1 or RNAi#2. Red: DISC1, Green: co-transfected GFP.

FIG. 3C Representative morphology of PC12 cells expressing RNAi#1, RNAi#2, or RNAi control with GFP.

FIG. 3D Percentages of PC12 cells harboring neurites 3 days after transfection of mock vector, RNAi control vector, RNAi#1, RNAi#2, wtDISC 1, mutDISC 1, or RNAi#1 with wtDISDC1 RNAi#1 effectively suppresses neurite outgrowth (#p<0.001, ##p<0.001). RiNAi#2 has a lesser effect compared with RNA#1. Furthermore, co-expression with wtDISC1 rescues neurite outgrowth from the effects of RNA#1 (*p<0.005). MutDISC1 has a similar effect to RNAi#2 at suppressing neurite outgrowth (**p<0.05).

FIG. 4A Western blotting of human autopsied brains, HeLa cells, and SH-SY5Y cells with an anti-DISC1 antibody (C2). DISC1 was expressed in two distinct bands at 95-100 kDa and 70-85 kDa in human brains. The signal from 70-85 kDa was subdivided into three categories: A major band in the middle at 75-85 kDa occurred in all the samples, with an additional upper signal in HeLa cells and a minor lower signal in HeLa cells and human brains. Similar results were obtained from antibodies from Drs. Millar and Katayama. FIG. 4B Mass spectrometry profile of the 75-85 kDa signal. The75-85 kDa protein was enriched by immunoprecipitation with an anti-DISC1-C2 antibody, and analyzed by mass spectrometry. The peptide fragments corresponding to DISC 1 were obtained, and correspond to SEQ ID NO:61 (OCGLDSR;position 85-91), SEQ ID NO:62 (SAAAPTVTSVR;position102-112), SEQ ID NO:63 (GGTRLPDR;position124-131), SEQ ID NO:64 (RDWLLQEK;position 455-462) and SEQ ID NO:65 (QQLQK;position 463-467).

FIGS. 5A-5B. A pool of DISC1 in the nucleus.

FIG. 5A DISC1 in the crude nucleus obtained by a classic method. In human autopsied brains, the DISC1 signal at 95-100 kDa was exclusively enriched in the postnuclear supematant (S), but the signal at 75-85 kDa occurred in both the crude nuclear pellet (P) and S fractions.

FIG. 5B DISC1 in a fraction enriched with nuclear transcription factors. In HeLa cells and SH-SY5Y cells, the major band at 75-85 kDa focused in the present study was distributed in both the nuclear fraction (N) and the cytosolic fraction (C). α-tubulin, and PARP were used for cytosolic and nuclear markers, respectively.

FIGS. 7a-7b. No change in the level of DISC1 in the total homogenates among patient brains with schizophrenia (SZ), bipolar disorder (BP), and major depression (MD) as well as control (NORM) brains. Relative ratios to the intensity of the band from one control sample were plotted. Dots represent the data from individual samples. Mean values ± SD were depicted.

FIG. 10A Exon/intron structure of DISC1 gene with the location and identification of SNPs studied here was depicted. NOVEL indicates the SNP we identified by the direct sequencing. The SNPs that lead to amino acid variation were indicated.

FIG. 10B The SNPs analyzed in this study. The identification number, location, and possible changes of deduced amino acid of each SNP were summarized. The physical location (bp) was based on build 34 of NCBI.

FIG. 10C Haplotype HP 1 and HP 2

FIG. 11B Expression of DISC1 at protein level in human lymphoblasts. DISC1 protein was analyzed in Western blotting by using two anti-DISC1 antibodies with independent epitopes, leading to similar results. The result of the antibody against the portion of DISC1 against 594- 854 amino acids was shown. Two distinct signals at 90-95 kDa and 70-80 kDa, indicated by arrows, were observed.

FIGS. 12A-12C DISC1 haplotype and gene expression: gender difference

FIG. 12A Comparison of DISC1 expression between affected subjects with the overtransmitted risk haplotype (BP-HP1) and unaffected with the undertransmitted haplotype (NON-HP2). Decreased DISC1 expression was observed in BP-HP1 compared with NON-HP2 (p=0.006).

FIG. 12B Comparison of DISC1 expression between BP-HP1 and NON-HP2 in female subjects. Marked decrease in DISC1 expression was observed in BP-HP1 (p=0.001).

FIG. 12C Comparison of DISC1 expression between BP-HP 1 and NON-HP2 in male subjects. No significant difference in DISC 1 expression was observed between two groups.

DETAILED DESCRIPTION OF THE INVENTION

Figure 1:
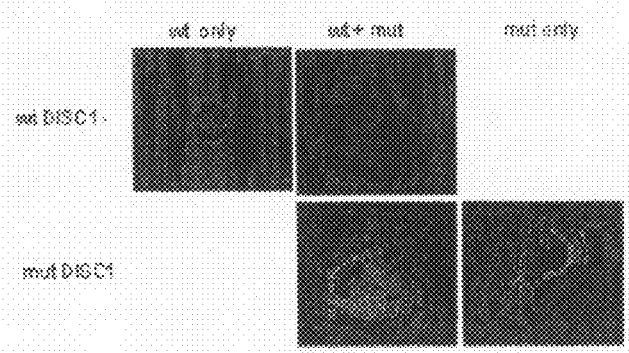
FIGS. 1A-1B Subcellular distribution of DISC1
Figure 1:
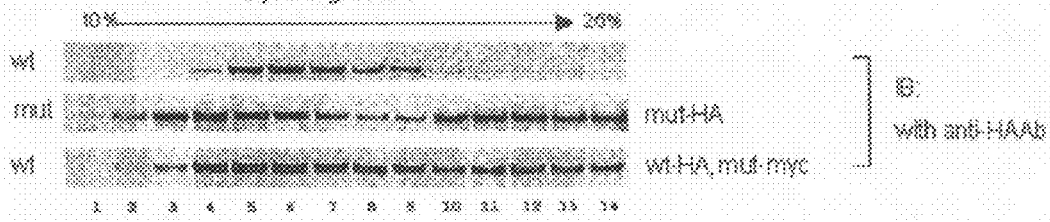

The present inventor has found that DISC1 protein could self-associate. Such self-association occurs between wtDISC1 and wtDISC1, mutDISC1 and mutDISC1 as well as wtDISC1 and mutDISC1.

The present inventor also found that mutDISC1 protein changes subcellular localization of wtDISC1. As a result, wtDISC1 loses its original subcellular distribution at the centrosome and displays a distribution almost equivalent to that of mutDISC1. This observation is confirmed by both cell staining and biochemical methods using glycerol gradient.

These results indicate that mutDISC1 functions as dominant negative, which mean loss of engdogeneous wtDISC1 function.

Further, the present inventor found that the suppression of wtDISC1 levels either by dominant negative function of mtDISC1 and/or RNAi leads to inhibition of neurite outgrowth.

The link between loss of DISC1 function and inhibition of neurite outgrowth indicates that the impaired function of DISC1 may be implicated for the microtuble actions.

DISC1 protein in a well-characterized set of autopsied brains, including brains of patients with schizophrenia, bipolar disorder, and major depression, as well as normal control brains were biochemically analyzed an isoform of DISC1 at 75-85 kDa was identified. Said isoform corresponds to DISC1 isoforms including exons 2 and 5.

Subcellular fraction of the isoform was examined and an increase in the ratio of the crude nuclear fraction (P fraction) to the postnuclear cytosolic fraction (S fraction) of DISC1 from brains of patients with SZ or those with substance abuse were observed. The P fraction excludes marker proteins from the cytosol, the mitochondria, and the postsynaptic density. The microtubules are recovered in both cytosolic and centrosome fractions, both of which are not enriched in the P fractions. In contrast, histone H1, a nuclear protein, is exclusively enriched in the P fraction. Accordingly, it can be concluded that the increase in the ratio of P to S fractions reflects the increase of DISC1 in the nucleus.

Considering the fact that total level of DISC1 unchanged, the increased levels of nuclear DISC1 may suggest the decrease in other pools of DISC1, especially in microtubles.

The inventor demonstrated that the levels of DISC1 expression at both mRNA and protein levels in lymphoblasts in bipolar disorder (hereinbelow "BP") subjects were lower than those in unaffected family controls. Based on association studies with DISC1, a haplotype over-transmitted to affected BP females, who showed lower levels of DISC1 expression was identified. Furthermore, correlation of clinical features of affected subjects to the levels of DISC1 expression was revealed.

In another aspect of the invention, a family-based association study of DISC1 and bipolar disorder in 57 bipolar pedigrees was conducted. In addition, DISC1 expression in human lymphoblasts at both mRNA and protein levels were examined. The correlation of several clinical features with the levels of DISC1 expression was studied.

Haplotype analysis identified one haplotype (HP1) that was overtransmitted to the BP phenotype (p=0.01) and a second haplotype that was undertransmitted (HP2). There was evidence of gender influence in the transmission distortion, with overtransmission of HP1 to affected females (p=0.004). There was a significant decrease in DISC1 expression in affected HP1 group compared to cell lines derived from unaffected subjects with the HP2 (p=0.006). This difference was more pronounced in females (p=0.001). Further, there is evidence to suggest that an earlier age of first manic episode and higher number of manic symptoms correlate with lower levels of DISC1 expression (p=0.008). Accordingly, it can be concluded that decreased levels of DISC1 expression, associating with the risk haplotype, may be implicated in the pathophysiology of bipolar disorder, especially in females.

Taken togeteher, these results can also suggest that decrease or loss of DISC1 function or levels can lead to psychiatric conditions.

EXAMPLES 1 and 2

Materials and Methods

Reagents and Antibodies

All reagents were from Sigma, Invitrogen except as indicated. Protein concentration was determined by using the BCA Protein Assay Reagent (PIERCE Biotechnology). Preparation of antibodies against DISC1 has been described (Ozeki et al., 2003). An affinity-purified rabbit antiserum against GFP (Molecular Probe) was used to visualize morphology of GFP-transfected PC12 cells in the neurite outgrowth assay. The vector system for shRNA was used to suppress endogenous DISC1 protein expression (Brummelkamp et al., 2002; Yu et al., 2002).

In this study, we produced 7 shRNA plasmids and selected two representative ones with the following sequences for the present study: RNAi#1 with strong suppression, 5'-GGCAAACACTGTGAAGTGC-3' (SEQ ID NO:1); RNAi#2 with milder suppression, 5'-CGGCTGAGCCAAGAGTTGG-3' (SEQ ID NO:2). Small oligonucleotides synthesized to the corresponding DISC1 sequences for siRNA were from Dharmacon RNA Technologies.

Cell culture, staining and neurite outgrowth assay

PC12 cells were maintained in Dulbecco's Modified Eagle Medium (DMEM) with 10% fetal bovine serum (FBS) and 5% horse serum (HS). Differentiation was initiated by the addition of 50 ng/ml of nerve growth factor (NGF) with culture medium changed to DMEM with 1% FBS and 1% HS. NGF was supplemented daily after differentiation. COS-7 and HeLa cells were maintained in DMEM with 10% FBS.

Transfection of expression constructs or RNAi constructs was carried out with Lipofectamine 2000 (Invitrogen) for PC12 cells, and COS-7 cells, and Polyfect Transfection Reagent (Qiagen) for HeLa cells.

Cell staining was carried out as described (Sawa et al., 1999). In brief, cells were fixed with 3.7% paraformaldehyde in PBS, and permeabilized with 0.1% Triton X-100. For some staining, ice-cold methanol at −20° C. was used as fixative.

Neurite outgrowth assay was performed as described (Ozeki et al., 2003). In brief, neurite outgrowth was evaluated by the percentage of cells with processes longer than three cell body diameters. The length of the longest process of each neurite-harboring cell was measured. In this study, we added a minor modification: to obtain clearer images of cell morphology, cells co-transfected with various expression or RNAi constructs with the GFP construct were stained with an anti-GFP antibody. A confocal microscope (Zeiss LSM 410) was used for epifluorescent image collections. A Zeiss Axiovert 135 microscope mounted with a charge-coupled device (CCD) camera (Roper Scientific CoolSnap HQ cooled 12 bit, Roper Scientific, Trenton, N.J.) was used to obtain PC12 cell images in the neurite outgrowth assay. Cell morphology was analyzed in a blinded manner. Statistical analyses were conducted by using a one-way ANOVA.

Biochemistry

Cell extraction: cells were homogenized or solubilized in ice-cold lysis buffer (0.32 M sucrose, 50 mM HEPES, pH 7.4, 5 mM $MgCl_2$, 5 mM 1,4-dithiothreitol (DTT), 1 mM phenylmethane sulfonylfluoride (PMSF), 1 mM EDTA, 1% Triton X-100, and a protease inhibitor mixture (Roche)). Immunoprecipitation: cells were lysed in a RIPA buffer (50 mM HEPES, pH 7.4, 150 mM NaCl, 5 mM $MgCl_2$, 5 mM DTT, 1 mM PMSF, 1 mM EDTA, 1% Triton X-100, protease inhibitor mixture), and supernatant fractions obtained after centrifugation at 10,000×g for 15 min were incubated with primary antibodies and protein A agarose (Oncogene). The immunoprecipitates were analyzed with SDS-PAGE followed by Western blotting. ProFound™ Mammalian HA Tag IP/Co-IP Kit and ProFound™ Mammalian Co-Immunoprecipitation Kit (PIERCE) were also used for immunoprecipitation.

In vitro binding assay: GST and His-tagged recombinant DISC1 protein fragments (amino acids 350-600) were incubated in 50 mM Tris-HCl, pH 7.4, 150 mM NaCl, and 0.1 mg/ml bovine serum albumin (BSA) for 1 h. His-tagged DISC1 bound to GST-tagged DISC1 was precipitated with glutathione Sepharose beads. The protein precipitates were analyzed with SDS-PAGE, followed by Western blotting with an antibody against His-tag.

Subcellular fraction was performed as described (Sawa et. al., 1997).

Glycerol Density Gradient Centrifugation and Centrosome Isolation

Cells with HA-tagged wtDISC1 and/or myc-tagged mutDISC1 were lysed in a buffer (20 mM HEPES, pH 7.4, 1% Triton X-100, 1 mM EDTA, 150 mM NaCl, 1 mM DTT, and protease inhibitor mixture), and centrifuged at 3,000×g for 10 min. The supernatant fractions were loaded on top of 4 ml of a 10-25% continuous glycerol gradient and centrifuged at 20,000×g for 24 h. Each fraction was analyzed by Western blotting with anti-HA or myc antibodies. Centrosome isolation was as described (Mohammed and Michel, 1998). Statistic analyses were conducted by using a one-way ANOVA followed by post hoc test.

EXAMPLE 1

Cellular Distribution of DISC1 Protein: Re-Distribution of wtDISC1 Protein in the Presence of mut DISC 1 Protein and Dominant Negative Function of mutDISC1

To examine the effect of mutDISC1, wt and mutDISC1 were expressed individually or together in COS-7 cells. wtDISC1 occurred selectively in the perinuclear regions, in contrast to the more diffuse cytoplasmic distribution of mutDISC1, as we and others have previouisly demonstrated (Morris et al., 2003; Ozeki et al., 2003). A significant change in subcellular distribution of wtDISC1 was observed upon co-expression of mutDISC1: wtDISC1 became distributed more diffusely in the cytoplasm (FIG. 1A). In contrast, the distribution of mutDISC1 was unchanged even after co-expression with wtDISC1. This result suggests that mutDISC1 disturbs the normal subcellular localization of wtDISC1; that is, it interferes with the normal and critical function of wtDISC1. This observation was confirmed by the glycerol gradient method (FIG. 1B) and subcellular fraction (data not shown).

DISC1 contains coiled-coil domains in the middle portion of the molecule, most of which are retained in mutDISC1. Thus, the inventor hypothesized that self-association of DISC1 might underlie the cellular effect of mutDISC1. To test this hypothesis, wt and mutDISC1 proteins with myc or HA-tag were expressed in HEK293 cells, and immunoprecipitates with an anti-myc antibody were analyzed. The results indicated that indeed DISC1 self-associated, and that mutDISC1 could bind to wtDISC1 (FIG. 2A). A series of DISC1 deletion mutants revealed that amino acids 403-536, which harbor a well-conserved colied-coil domain, are essential for DISC1 self-association (FIG. 2B). Exogenous mut- DISC1 in differentiated PC12 cells is co-immunoprecipitated with endogenous DISC1 (Supplemental FIG. 2). The self-association is as the result of its direct protein interaction, as confirmed by in vitro binding experiments with purified glutathione-S-transferase (GST)- and His-tagged DISC1 proteins (FIG. 2C).

Taken together, these results suggest that mutDISC1 acts in a dominant-negative fashion by associating with wtDISC1.

EXAMPLE 2

Confirmation of functional alteration of DISC1 by using "Newrite Outgrowth Assay"

The inventor has already reported that transient overexpression of mutant DISC1 in PC12 cells reduces neurite extension. In the present invention, we introduced RNA interference (RNAi) technique to modulate the expression levels of endogenous DISC1 protein in PC12 cells, and succeeded to reduce its expression. Plasmids encoding short hairpin RNA (shRNA) against several portions of DISC1 were tested, and two representative ones were chosen for the following functional studies: the strong suppressor (RNAi#1) and milder suppressor (RNAi#2). Their potency was initially tested with Western blotting in HeLa cells co-transfected with the expression construct of rat DISC1 and a DISC1 RNAi plasmid, which did not interfere with endogenous human DISC1. RNAi#1 and RNAi#2 displayed 90 and 40% suppression against rat DISC1, respectively, when compared with sets of control RNAi plasmids containing unrelated sequences (FIG. 3A). Marked suppression of endogenous DISC1 by RNAi#1 was confirmed in differentiated PC12 cells by immunofluorescent cell staining (FIG. 3B) as well as Western blotting (data not shown). Synthetic oligonucleotides for small interfering RNA (siRNA) with the DISC1 sequences corresponding to RNAi#1 and #2 led to similar results (data not shown). We observed dramatic inhibition of neurite outgrowth in differentiating PC12 cells with the strong suppressor, RNAi#1 (FIGS. 3C, D) The disturbance of neurite outgrowth was unrelated to cell death and no signs of apoptotic nuclei were observed in cells with RNAi (data not shown). The effect of RNAi was correlated with the levels of DISC1 suppression, as RNAi#1 showed a much more marked inhibition of neurite outgrowth than did RNAi#2. As co-transfection of the expression construct of wtDISC1 normalized the inhibition of neurite outgrowth by RNAi#1, the effect of DISC1 RNAi could be attributed to the direct suppression of DISC1 (FIG. 2D). Suppression of DISC1 or overexpression of mutDISC1 both impair neurite outgrowth, consistent with the notion that mutDISC1 functions in a dominant negative fashion (FIG. 2D).

EXAMPLE 3

A Form of DISC1 Enriched in the Nucleus has Altered Subcellular Distribution in Schizophrenia Brains Materials and Methods Brains. Human postmortem orbital cortices from normal controls as well as patients with schizophrenia, bipolar disorder (BP), and major depression (MD) were obtained from the Stanley Foundation Brain Collection. Each group had 15 subjects. Detailed information of the original set of subjects has been previously described (Torrey et al 2000).

Chemicals. All reagents were purchased from Sigma (St. Louis, Mo.) except as indicated. Protein concentrations were determined by using the bicinchoninic acid protein assay kit (Pierce, Rockford, Ill.).

Antibodies. Preparation of an immuno-purified anti-DISC1 antibody was described previously (Ozeki et al 2003). In brief, the antibodies were raised against a portion of DISC1 (601-854 (C2)) tagged to glutathione S-transferase. The dilutions of antibodies used in this study were as follows: DISC1-C2, 1: 250; Histone H1 (Santa Cruz biotechnology, Santa Cruz, Calif.), 1: 100; poly-ADP polymerase (PARP) (BD Biosciences Pharmingen, San Diego, Calif.), 1:250; PSD95 (Zymed Laboratories, South San Francisco, Calif.), 1:500; γ-tubulin (Sigma, St, Louis, Mo.), 1: 10,000; α-tubulin (Sigma, St, Louis, Mo.), 1:4,000; cytochrome c oxidase (Molecular Probes, Eugene, Oreg.), 1: 50; and glyceraldehyde-3-phosphate dehydrogenase (Sawa et al 1997), 1: 2,000.

Mass spectrometry. HeLa cells were lysed in RIPA buffer (150 mM NaCl, 10 mM Tris-HCl, pH 7.5, 1% Nonidet P-40, 0.1% SDS, and 0.5% sodium deoxycholate) containing a protease inhibitor (Complete™) (Roche Applied Sciences, Indianapolis, Ind.), mixture. The solubilized proteins were subjected to immunoprecipitation as described previously (Sudoh et al 1998) using anti-DISC1-C2 antibody (11), and the precipitated proteins were subjected to SDS-PAGE. The major band of DISC1 at 75-85 kDa was visualized by Coomassie staining. Gel-purified DISC1 at 75-85 kDa was tryptic digested and analyzed by MALDI-TOF mass spectrometry (Voyger DE STR, Applied Biosystems) in the mass spectrometry facility at Johns Hopkins University School of Medicine. Peptide Mass was analyzed using the programs Peptide Mass (http://au.expasy.org/tools/peptide-mass.html) and MS-Digest (http://prospector.ucsf.edu/ucsfhtml4.0/msdigest.htm).

Subcellular fraction. A classic method of subcellular fraction was used for autopsied human brains and HeLa cells (Sawamura et al 2001, Gu et al 2001). In brief, 0.1 g of tissues or cells were homogenized in a ice-cold buffer (50 mM Tris-HCl, pH 7.4, 150 mM NaCl, Protease inhibitors (Complete™), using a motor-driven Teflon homogenizer. The homogenates containing equal amounts of protein were centrifuged at 800×g for 10 min at 4° C. to obtain a crude nuclear pellet (P) and postnuclear supernatant (S).

For further analysis of nuclear fractions, we used a standard protocol to enrich for transcription factors with minor modifications (Andrews et al 1991, Hua et al 1996). Cell homogenates from HeLa and SH-SY5Y cells were lysed in buffer A (10 mM HEPES, pH 7.9, 1.5 mM MgCl2, 10 mM KCl, 1 mM DTT, and protease inhibitors (Complete™) were centrifuged at 2,300×g for 2 min at 4° C. The pellet was resuspended in buffer A containing 0.1% Nonidet-P, centrifuged at 1,500×g, and the cytoplasmic supernatant was collected. The pellet was resuspended in buffer C (20 mM HEPES, 25% glycerol, 420 mM NaCl, 1.5 mM. MgCl2, 1 mM DTT, and protease inhibitors (Complete™) were centrifuged at 16,000×g for 15 min at 4° C. The final supernatant is considered to be a nuclear fraction with enriched in transcription factors (Andrews et al 1991, Hua et al 1996).

Western blotting. A standard protocol previously described was employed with minor modifications (Sawamura et al 2004). Proteins were separated using Novex Tris-Glycine gel (Invitrogen, Carlsbad, Calif.) and transferred onto a polyvinylidene difluoride (PVDF) membrane (Millipore, Bedford, Mass.). Nonspecific binding was blocked with 5% fat-free milk in phosphate-buffered saline containing 0.1% Tween 20. The blots were then incubated with primary antibodies overnight at 4° C. For the detection of both monoclonal and polyclonal antibodies, appropriate peroxidase-conjugated secondary antibodies were used in conjunction with enhanced chemiluminescence (Amersham Biosciences, Piscataway, N.J.) to obtain images saved on film.

Statistical analysis. Statistical analysis was carried out using Stat View computer software (Macintosh, version 5.0; Abacus Concepts Inc., Berkeley, Calif.). One-factor analysis of variance (ANOVA) was used for the initial assessment among groups. When a significant difference was obtained, post hoc comparison with the Bonferroni-Dunn test was used to identify the specific group differences.

The influence of demographics and other variables from brains from the Stanley Foundation on DISC1 was examined by Pearson's correlation coefficients for continuous variables as well as by two-tailed Student's t-test or one-factor ANOVA for categorical variables. Post hoc comparison with Tukey-Kramer test and two-tailed Student's t-test was used to examine differences among the specific groups. Probability values (p value) below 0.05 were considered to be statistically significant. All values were described as means and standard deviation (SD).

Results 3.1 DISC1 protein in human autopsied brains.

Figure 4:
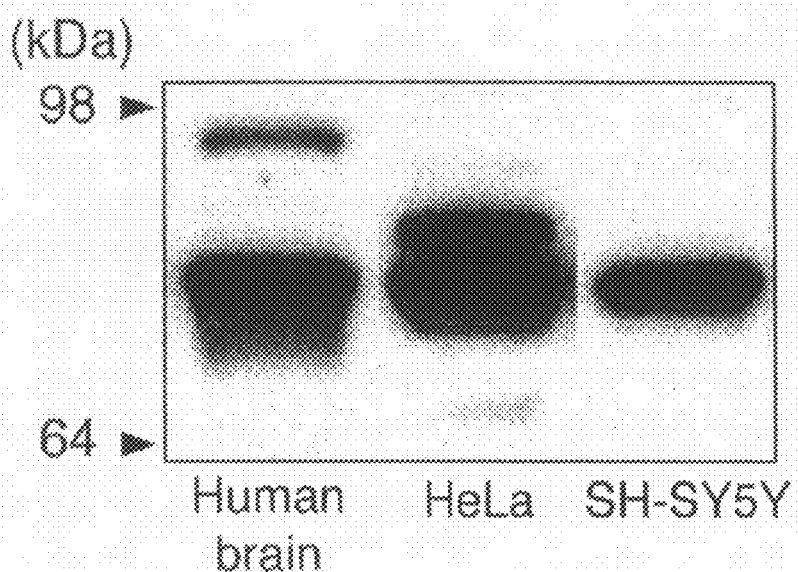
FIGS. 4A-4B. Characterization of human DISC1 protein.

Protein expression of DISC1 in human autopsied brains was analyzed by Western blotting, and compared with that in human cell lines of HeLa and SH-SY5Y cells (FIG. 4A). DISC1 is expressed in two distinct bands at 95-100 kDa and 70-85 kDa in human brains, which resembles the profiles in rodent brains previously reported by our group and others (Miyoshi et al 2003, Ozeki et al 2003, Brandon et al 2004). Similar to rodent brains, the signal at 70-85 kDa was much more intense than that at 95-100 kDa. The signal at 95-100 kDa has been thought to represent authentic full-length DISC1, as it is detected by multiple antibodies against DISC1, with the expected protein size of 854 or 832 amino acids from DISC1 open reading frame (Miyoshi et al 2003, Ozeki et al 2003, James 2004). In contrast, the molecular identify of the 70- 85 kDa signal still remained elusive.

The signal from 70-85 kDa was subdivided into three categories (FIGS. 4A, 5). A major band in the middle at 75-85 kDa occurs in human brains, HeLa, and SH-SYSY cells. An upper signal was observed in HeLa cells and a minor lower signal in HeLa cells and human brains. In the present study, we focused our analyses on the major signal at 75-85 kDa. To characterize the 75- 85 kDa signal directly, we used HeLa cell extracts with protein chemistry that combined immunoprecipitation and mass spectrometry. Immunoprecipitation of HeLa cells with an anti-DISC1 antibody leads to enrichment of the 75-85 kDa signal to the levels detectable by Coomassie staining (data not shown). The enriched protein was analysed on SDS-PAGE, excised from the gel, and digested with trypsin. The obtained fragments were analysed by mass spectrometry. We found five independent fragments that were derived from DISC1 sequences from the profiles of mass spectrometry (FIG. 4B). No signal corresponding to DISC1 was obtained when we used pre-immune sera for the immunoprecipitation (data not shown).

3.2 Nuclear Enrichment of a Form of DISC1.

Previous reports have suggested that DISC1 may have more than one subcellular pool (Miyoshi et al 2003, Ozeki et al 2003, Morris et al 2003, James et al 2004). DISC1 contains evolutionally well-conserved nuclear localization signals in the open reading frame (Ma et al 2002), suggesting its potential role in the nucleus. Thus, we conducted subcellular fraction, paying particular attention to its possible nuclear pool.

Figure 6:
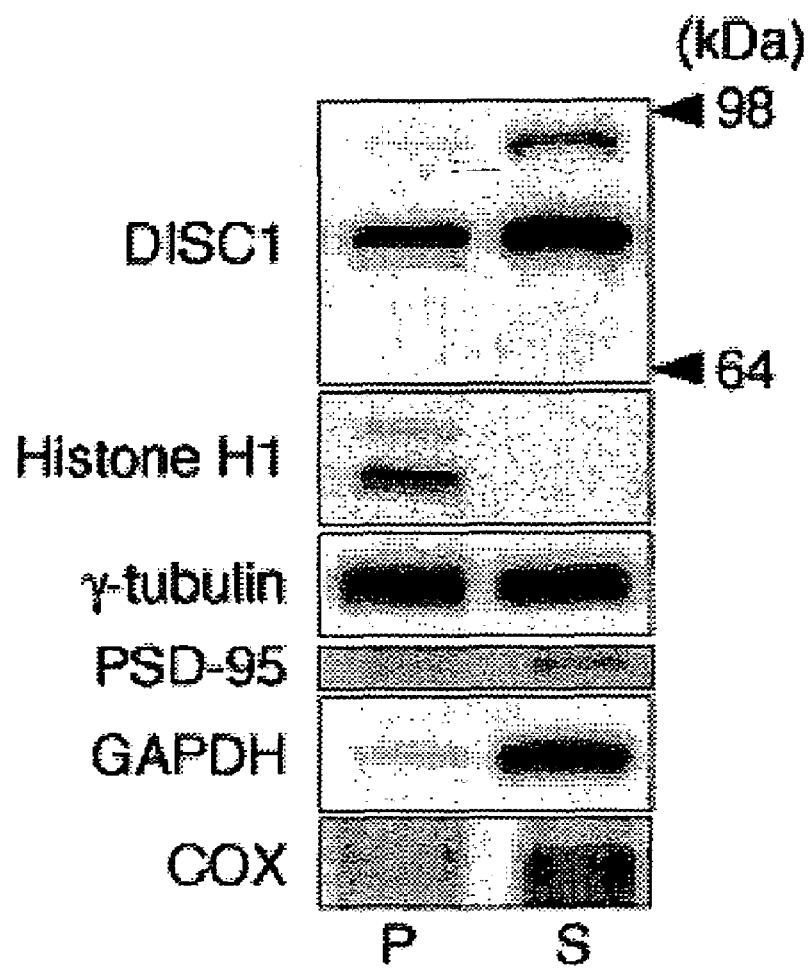
FIG. 6. Characterization of the P and S fractions from human autopsied brains by a variety of organelle markers. The markers for cytoplasm (GAPDH), mitochondria (cytochrome c oxidase, COX), postsynaptic density (PSD) occur almost exclusively in the S fraction. In contrast, Histone H1, a nuclear protein, is exclusively enriched in the P fraction. g-tubulin, the centrosome marker, is recovered almost equally in the S and P fractions.

A classic method of subcellular fraction (Sawamura et al 2001, Gu et al 2001) was used for an initial estimation. In human autopsied brains, the DISC1 signal at 95-100 kDa was exclusively enriched in the postnuclear supernatant (S), but the signal at 75-85 kDa occureed in both the crude nuclear pellet (P) and S fractions (FIGS. 5A). DISC1 at 75-85 kDa occurs in both the P and S fractions. We further characterize the S and P fractions from human autopsied brains by variety of organelle markers (FIG. 6). The markers for cytoplasm, mitochondria, and postsynaptic density occur almost exclusively in the S fraction In contrast, Histone H1 is exclusively enriched in the P fraction. v-tubulin is recovered almost equally in the S and P fractions. In conclusion, the P fraction is an enriched nuclear fraction, with some contamination of the centrosome. These results suggest that a form(s) of DISC1 at 75-85 kDa may exist in the nucleus.

To obtain further information about nuclear DISC 1, we used an established protocol for enrichment of nuclear transcription factors (Andrews et al 1991, Hua et al 1996). In HeLa and SH-SY5Y cells, substantial enrichment of a form(s) of DISC1 at 75-85 kDa was observed in the nuclear fractions (FIG. 5B).

3.3 Aberrant Subcellular Distribution of DISC1 in Brains from Patients with Major Mental Illnesses.

To analyze the disposition of DISC1 in human brains, especially in brains from patients with psychiatric conditions, we used the well-characterized brain sets from the Stanley Foundation Brain Collection (Torrey et al 2000). The brain set contains four groups of brains from 15 normal subjects, 15 patients with SZ, 15 patients with bipolar disorder (BP), and 15 patients with major depression (MD).

First, we addressed the levels of DISC1 protein in total brain homogenates. No significant differences in the total levels of DISC1 protein among four groups were observed in both 95-100 kDa and 75-85 kDa signals (p=0.5093 and 0.2409, respectively by one-factor ANOVA) (FIG. 7).

Figure 8:
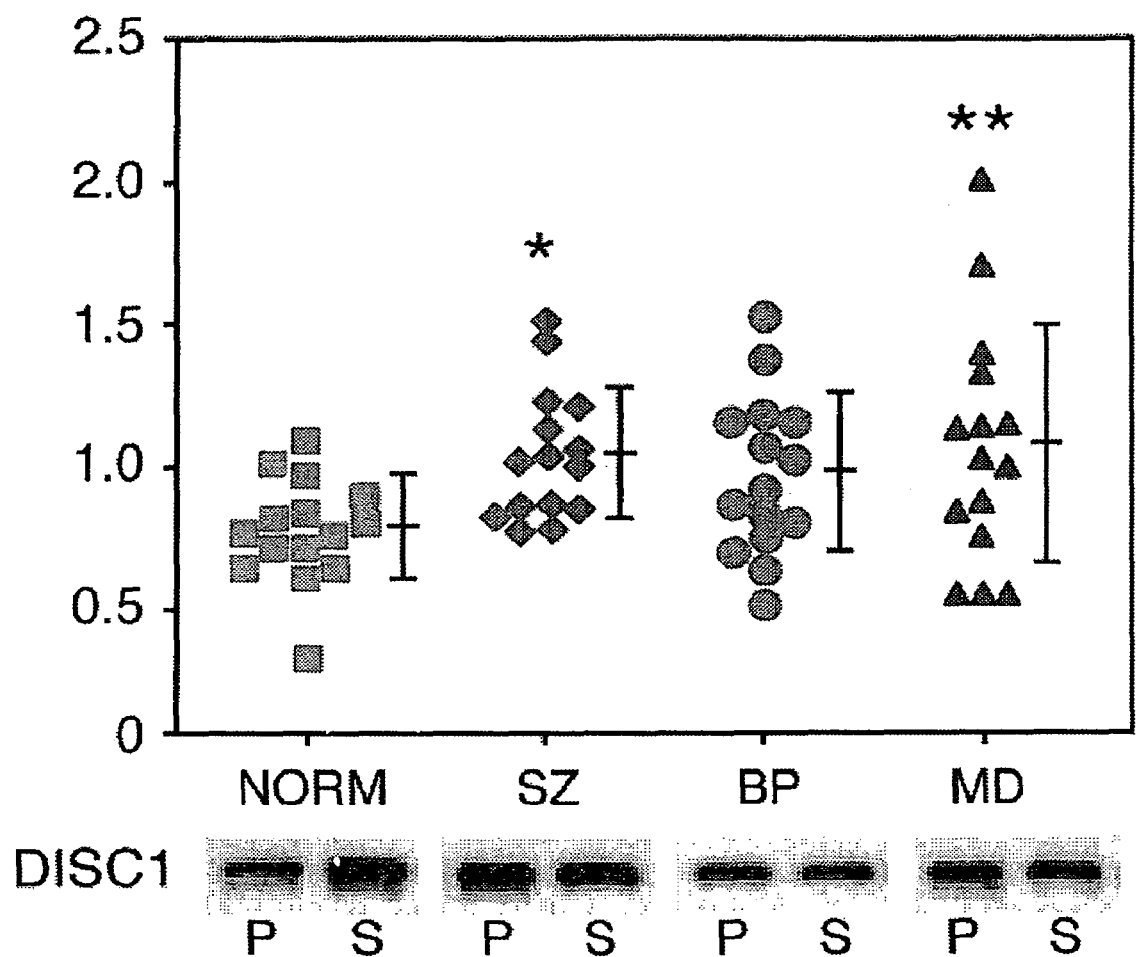
FIG. 8. Aberrant subcellular distribution of DISC1 in patient brains with SZ and MD. Subcellular distribution of DISC1 in human brains was analyzed using the protocol of subcellular fraction, which was characterized in FIGS. 5A and 6. The signal ratio of DISC1 from the P fraction to the S fraction (the P: S ratio) was increased in patient brains with SZ and MD group (p=0.018 and 0.009, respectively). Dots represent the data from individual samples. Mean values ± SD were depicted.

Second, we focused on subcellular distribution of DISC1 in these brains. To evaluate semi-quantitatively the fraction of DISC1 in the crude nucleus, we examined the signal ratio of DISC 1 at 75-85 kDa from the P fraction compared to the S fraction (the P:S ratio) in the subeellular fraction that was characterized above (FIG. 5A and FIG. 6). Of interest, a significant difference in the P:S ratio is observed among the four groups (p=0.0398 by one-factor ANOVA). Post hoc comparison by using the Bonferoni-Dunn test reveals that the P:S ratio in SZ and MD groups are significantly increased in comparison with that of the control group (p=0.018 and 0.009, respectively) (FIG. 8).

Figure 9:
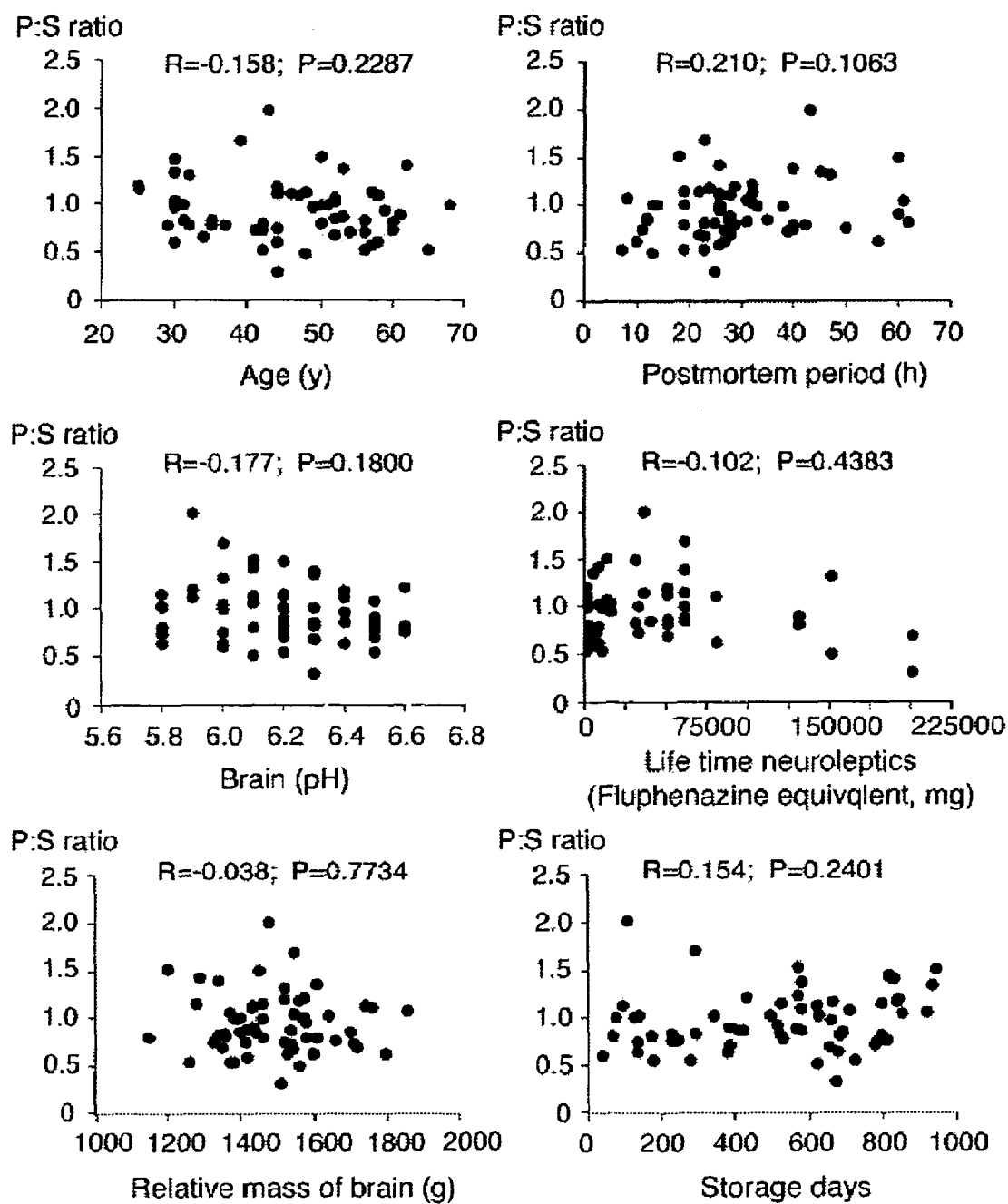
FIG. 9. The P:S ratio of DISC1 was not influenced by postmortem delay, brain pH, and storage time of frozen brains, age at sample collection, life-time dosage of neuroleptics, and relative mass of brain.

The P: S ratio seems not to be influenced by the process used to obtain autopsied brains, as evidenced by no effects of postmortem delay, brain pH, and storage time of frozen brains (FIG. 9). Age at sample collection, life-time dosage of neuroleptics, and relative mass of brain also have no effects on the ratio (FIG. 9).

3.4 Influence of Substance Abuse on Subcellular Distribution of DISC1 in Autopsied Brains.

Furthermore, this P: S ratio of DISC1 is significantly associated with the history of substance abuse (p=0.0005) (Table 1). To examine whether the increases in the ratio in SZ and MD groups are influenced by histories of substance abuse, Tukey post hoc test was performed for all four groups. The increase in the ratio in SZ is unrelated to current substance abuse, but the increase in the ratio in BP is related to substance abuse (p<0.05).

The P: S ratio is also significantly associated with severity of substance abuse (p=0.002) (Table 1). The impact of the severity of substance abuse on the P: S ratio was tested by unpaired t-test. There is no impact of the severity on the ratio in SZ, but in MD, is significantly influenced (p=0.433).

Effect of gender, Hemisphere, Psychosis, substance abuse, and alcohol abuse on P:S ratio.

| Parameter | Groups | Mean ± SD | P value |
|---|---|---|---|
| Gender | Male (n = 36) | 0.939 ± 0.317 | 0.444 (t-test) |
| | Female (n = 24) | 1.002 ± 0.297 | |
| Hemisphera | Right (n = 27) | 0.867 ± 0.260 | 0.026* (t-test) |
| | Left (n = 33) | 1.044 ± 0.325 | |
| Psychosis | With (n = 26) | 1.021 ± 0.246 | 0.212 (t-test) |
| | Without (n = 34) | 0.920 ± 0.246 | |
| History of substance abuse | Never (n = 37) | 0.865 ± 0.217 | 0.0005*** (one-factor ANOVA) |
| | Past (n = 8) | 0.953 ± 0.214 | |
| | Current (n = 15) | 1.215 ± 0.402 | |
| Severity of substance abuse | Lowest (n = 41) | 0.890 ± 0.221 | 0.002** (one-factor ANOVA) |
| | Lower (n = 1) | 0.550 | |
| | Low (n = 2) | 0.880 ± 0.028 | |
| | High (n = 6) | 0.970 ± 0.328 | |
| | Higher (n = 4) | 1.215 ± 0.297 | |
| | Highest (n = 5) | 1.388 ± 0.525 | |
| Severity of alcohol abuse | Lowest (n = 13) | 0.835 ± 0.198 | 0.065 (one-factor ANOVA) |
| | Lower (n = 19) | 0.888 ± 0.265 | |
| | Low (n = 4) | 0.837 ± 0.293 | |
| | High (n = 7) | 0.991 ± 0.268 | |
| | Higher (n = 4) | 1.018 ± 0.187 | |
| | Highest (n = 6) | 1.265 ± 0.507 | |

EXAMPLE 4

Differential expression of DISC1 in bipolar disorder: evidence of sex effect

Subjects

The research subjects for this study were taken from a large ongoing linkage study in BP (McInnis et al 2003). Briefly, these multiplex pedigrees (the Hopkins/Dana pedigrees) were ascertained on the presence of a treated BPI proband with 2 affected first-degree relatives, affection status included BPI, BPII, recurrent major depression, and schizoaffective disorder, manic type. The recent genome-wide scan of these pedigrees identified a susceptibility locus on 1q41, the peak marker, D1S549 was 12 Mb centromeric from the DISC1 gene, however the region of significance is broad and encompasses the DISC1 gene. Similarly, the 1q42 peak identified by Macgregor et al (Macgregor et al 2004) was centromeric from DISC1.

From the larger collection, there were 57 BP pedigrees selected for genotyping. The selection aimed to include pedigrees with either both parents present, or pedigrees that included an unaffected sibling as well as 2 affected siblings. Therefore, there were up to 5 subjects typed from each family. The total sample consisted of 297 subjects genotyped and is described in detail in Table 2.

TABLE 2

Subjects (57 families) in this study: originally ascertained for genetic linkage analyses

| | Total | Male | Female |
|---|---|---|---|
| BPI[a] | 62 | 29 | 33 |
| BPII[b] | 50 | 24 | 26 |
| RUP[c] | 35 | 12 | 23 |
| SAM[d] | 5 | 3 | 2 |
| Unaffected | 64 | 26 | 38 |
| Uncertain | 81 | 46 | 35 |
| Total | 297 | 140 | 157 |

[a]Bipolar I
[b]Bipolar II
[c]Recurrent unipolar disorder
[d]Schizoaffective manic Direct Sequencing DNA from 10 bipolar subjects was chosen to identify polymorphisms in the DISC1 gene. They were selected from pedigrees with the strongest evidence for linkage to chromosome 1q42, based on the output from GENEHUNTER. Each coding exon of DISC1 with 50 bp of flanking intron was amplified using primers described in table 3A. Exon 2 was too large to be amplified by a single PCR reaction, and was subsequently sequenced in 3 reactions. Most of PCR condition were the following: 80 ng of genomic DNA, 0.4 µM of each primer, 400 µM dNTPs, 1.5 mM $MgCl_2$, 1 unit TaqDNA polymerase (invitrogen), 2.5 µl of a PCR buffer (200 mM Tris-HCl, 500 mM KCl) and up to 25 µl with sterile water. An initial denaturation step of 94° C. for 7 min was followed by 40 cycles of 94° C. for 45 sec, 55° C. for 30 sec and 72° C. for 30 sec. Detailed information for amplification is available upon request. The resulting of PCR products were purified by spin column (QIAGEN) and were preformed with BigDye Terminator cycle sequencing kit (Applied Biosystems). The purified products were sequenced using ABI PRISM 370

DNA sequencer (Applied Biosystems). The sequences were aligned using Sequencher (Gene Codes Corporation).

Genotyping

All samples were genotyped by using a 5' exonuclease assay (TaqMan) and the ABI 7900HT sequence detection system (Applied Biosystems). For 6 single nucleotide polymorphisms (SNPs) (rs1538975, rs1954175, rs1407598, rs1000731, rs821653, rs3524) we used assays-on-Demand kits, and for the remaining of 6 SNPs we ordered custom made, Assays-by-Design kits. The sequence information of the primers and probes in this assay is described in Table 3B. Assays (25 μl) were carried out on about 10 ng genomic DNA according to manufacture's instructions. PCR reactions were done on GeneAmp PCR system 9700 and fluorescence signals were detected on ABI 7900HT.

TABLE 3

Primer information used in the study

A. Primer sequencing for direct sequencing

| Exon | product size | Forward primer sequence (5'-3') | Reverse primer sequence (5'-3') |
|---|---|---|---|
| 1 | 331 | GAC TCG CTG AGG AGA AGA AAG (SEQ ID NO:3) | GGT TGT TAA CAG AGG CAC GC (SEQ ID NO:4) |
| 2 part 1 | 458 | TTC TCC AGA TGC AGT TCC AGC (SEQ ID NO:5) | TAT CCA TGG CTG CAA ACT CTT (SEQ ID NO:6) |
| 2 part 2 | 496 | CAG CCC CTA CTG TGA CCT CTG T (SEQ ID NO:7) | AAG ACT GAA GGG CCG AGA GAG AC (SEQ ID NO:8) |
| 2 part 3 | 485 | GAA CGT GGA GAA GCA GAA GG (SEQ ID NO:9) | GGA AGT CAG TTG AGC CCA GA (SEQ ID NO:10) |
| 3 | 283 | GAA ACT AAT GCA TCT GGC ATT GA (SEQ ID NO:11) | TGG GAC ATG ATG ACA AAA CAA T (SEQ ID NO:12) |
| 4 | 253 | CAC CGG GGT TAT CTA TTT TGC AT (SEQ ID NO:13) | TGA GGG GAA AAT GGT GAC AAT A (SEQ ID NO:14) |
| 5 | 250 | CAT GAG GAT TTC AGC TTC TGC (SEQ ID NO:15) | GCA AGA CCC TGT CTC AAA GAA (SEQ ID NO:16) |
| 6 | 394 | GGT GCA TAT GGC CAA TTC TC (SEQ ID NO:17) | CCA ATG AAC AGG TCA AAG AGG (SEQ ID NO:18) |
| 7 | 242 | GTG GAA GGT TCA CTT TTT GCA G (SEQ ID NO:19) | TGC AGA AGC CAG GTA TCC TAA G (SEQ ID NO:20) |
| 8 | 249 | AAT CTC TGA CCT GGC TGT TCC (SEQ ID NO:21) | ACG ATG TGC TGG TAG CTG TCA T (SEQ ID NO:22) |
| 9 | 285 | TCT TCC ATG TGT GTG GAT GCT G (SEQ ID NO:23) | ACT TTG CCG GGG AAC AGT TG (SEQ ID NO:24) |
| 10 | 248 | TCA ATC CTT TGG CTT TGA GCT T (SEQ ID NO:25) | CTG GCC AGC CTT TTT CAT CG (SEQ ID NO:26) |
| 11 | 388 | AGC CAG GTA GAC AAG CTA TCG (SEQ ID NO:27) | GAA TAA GGG TCC CCT CTG GAG (SEQ ID NO:28) |
| 12 | 252 | GTC CAC GGC ACT AAC AAG TGA T (SEQ ID NO:29) | CCA TCT TCT GAG GCA TGA AAA AC (SEQ ID NO:30) |
| 13 | 291 | AGA GGG CCA CGA TCA CCT TC (SEQ ID NO:31) | ATC TCC GTA ATT GAT TCA GGC A (SEQ ID NO:32) |

B. Primers and probes in the TaqMan assays

| Forward primer sequence (5'-3') | Reverse primer sequence (5'-3') | VIC Probe sequence (5'-3') | FAM Probe sequence (5'-3') |
|---|---|---|---|
| ACGAGGACCCGCGATG (SEQ ID NO:33) | ACCCGTGTAGCCAAGAGACT (SEQ ID NO:34) | TCTCTCTCAGCCCTTC (SEQ ID NO:35) | TCTCTCGGCCCTTC (SEQ ID NO:36) |
| CAGGCCGCAAGGAACAG (SEQ ID NO:37) | GGTCCATGTCTGGTAAAGAAT GCA (SEQ ID NO:38) | ACGCTCTGGCCTGG (SEQ ID NO:39) | CACGCTCTAGCCTGG (SEQ ID NO:40) |
| CCCTCAACTTGTCACTTAAAG AAATCAC (SEQ ID NO:41) | AGTCAAACGAAAACTTCATAG GCTTCT (SEQ ID NO:42) | AAAATGGGAATATAAAG GTACTTA (SEQ ID NO:43) | AATGGGAATATAAAGGTG CTTA (SEQ ID NO:44) |

TABLE 3-continued

Primer information used in the study

| CAACGTGCTGTAGGAAACCAT TT (SEQ ID NO:45) | CAGCCCTTCTCTCTCTGATGT TAAT (SEQ ID NO:46) | CTCGGTGAGGTCTTTA (SEQ ID NO:47) | TCGGTGAAGTCTTTA (SEQ ID NO:48) |
|---|---|---|---|
| GACTTGGAAGCTTGTCGATTG C (SEQ ID NO:49) | GCTTCCCCTGGCTTCCT (SEQ ID NO:50) | CTGTAGGCACTGGATAA (SEQ ID NO:51) | CTGTAGGCTCTGGATAA (SEQ ID NO:52) |
| TGCTGAATTTCCTTCTAAATG TCACTCA (SEQ ID NO:53) | AATTCACCCCAACTTCTCTCT AATGG (SEQ ID NO:54) | ATTCTTGGGAATGTC (SEQ ID NO:55) | CATTCTTGAGAATGTC (SEQ ID NO:56) |

C. Primers for RT-PCR

| Exons | Forward primer sequence (5'-3') | Reverse primer sequence (5'-3') |
|---|---|---|
| 4-5 | ACGCGTCGACCCAGCCAGCTCTTAGCAGTTTC (SEQ ID NO:57) | AACAGCCTCGGCTCCATTCTC (SEQ ID NO:58) |
| 8-9 | GCACCCTGAGGAAGAAAGTT (SEQ ID NO:59) | TCTCTTCTCAGTCTGTTGTAATCT (SEQ ID NO:60) |

Genetic Analysis and Statistics

Inter-marker LD and haplotype block structure were examined using the program Haploview. Association tests were then performed using the computer program FBAT (Family Based Association Test) (Horvath et al 2001). FBAT was chosen because it provides valid tests of association in the presence of linkage even when using multiple affected siblings from families of variable structure. In addition to performing tests of association for individual markers, FBAT allows for tests of association with haplotypes that may be phase ambiguous.

Expression Analysis

Lymphoblasts from patients were established with infection of Epstein Barr virus (Sawa et al 1999). Cells were maintained in RPMI1640 media with 10% fetal bovine serum, and used within 2 weeks (4 cycles of cell division) for expression analyses.

Expression of DISC1 was initially verified by RT-PCR with two sets of primers. To avoid the contamination of the amplification from genomic DNA, each pair was chosen from two independent exons (Sawa et al 1997). The primer sequences are described in Table 3C.

Expression levels of DISC1 in lymphoblasts were measured by the RNA counter kit (TrimGen, Sparks, Md.). This kit employs the isometric primer extension technology. A portion of DISC1 including both exons 6 and 7 (nucleotides 1627-1647 in the NCBI AF22980) was amplified from total RNA. The amplification over two independent exons avoids contaminated signals from genomic DNA. The amplified region was selected because this includes no genetic variability or SNP. Actin was used for an internal control of expression.

Western blotting was carried out as described (Ozeki et al 2003). Two antibodies against different portions of DISC1 (one for amino acids 354-597, the other for 598-854) were used (Ozeki et al 2003).

Clinical Data Analysis

Using the statistical software, STATA, clinical features of affected subjects with DISC1 expression data were analyzed. The broad affection status model (including BPI, BPII, recurrent major depression, and schizoaffective disorder manic type) was used for definition of affection. Linear regression was used to model DISC1 expression levels as a dependent variable in relation to various clinical features of the affected subjects.

Result 4.1 Family-Based Association Study

Figure 10:
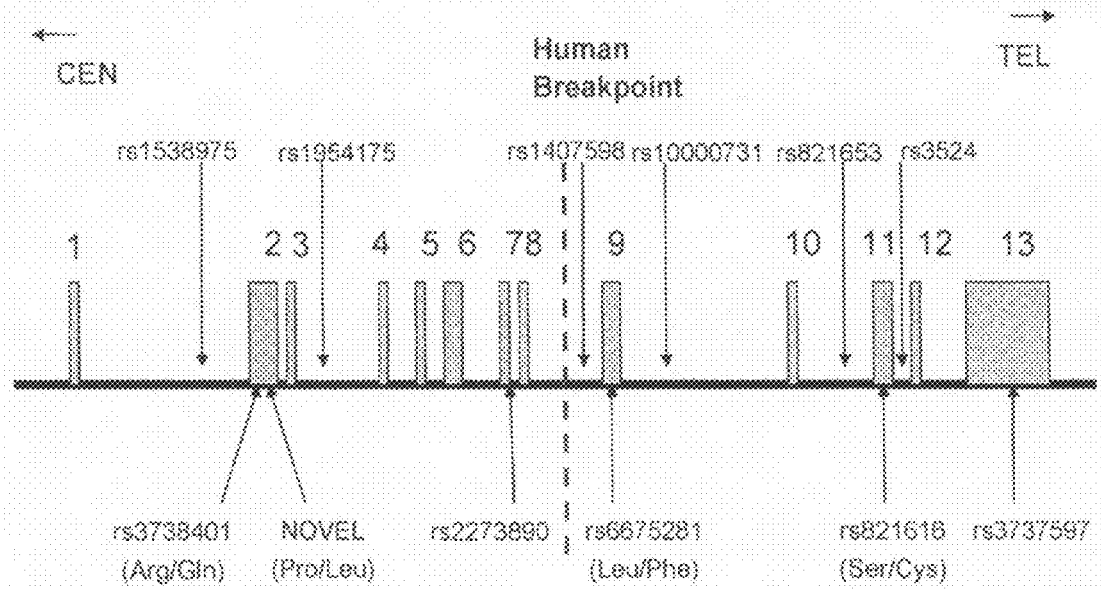
FIGS. 10A-10C. Schematic presentation of SNPs in DISC1 gene

Sequencing of the exons from 10 probands taken from the pedigrees with most evidence of linkage identified one novel SNP (FIGS. 10A-10B). This SNP was typed in the subset of 58 BP pedigrees. Using the algorithm of Gabriel et al (Gabriel et al 2002), as implemented in Haploview, there were 3 haplotype blocks in this gene spanning approximately 200 kb. Analysis of the individual markers identified no significant association with BP disorder. Haplotype analyses using FBAT and all 12 markers identified two haplotypes with frequencies of 0.11 (H1) and 0.10 (H2). We tested several individual SNPs and various combinations of SNPs for possible haplotypes, and obtained the significance only from the total 12 marker haplotype. H1 was overtransmitted to the affected subjects (p=0.01) and H2 was undertransmitted. When considering the sex of the affected subjects, it was clear that the overtransmission was to the affected females (p=0.0044) (Table 4), there was no evidence of overtransmission of H1 to the affected males.

TABLE 4

Genetic transmission of the inclusive 12 marker haplotype of those markers outlined in FIG. 1

| | Total | | Female | | Male | |
|---|---|---|---|---|---|---|
| | $z^a$ | $p^b$ | z | p | z | p |
| HP1 | 2.6 | 0.01 | 2.8 | 0.004 | 0.7 | 0.5 |
| HP2 | -1.7 | 0.08 | -1.1 | 0.3 | -1.9 | 0.06 |

[a] z distribution
[b] p value 4.2 DISC1 Expression in Human Lymphoblasts

Figure 11:
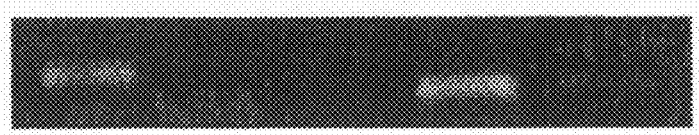
FIGS. 11A-11B DISC1 expression in human lymphoblasts at mRNA and protein levels FIG. 11A Expression of DISC1 at mRNA level in human lymphoblasts. Independent portions of DISC1 (between exons 4 and 5 as well as exons 8 and 9) were amplified by RT-PCR from both HeLa cells and human lymphoblasts (LB). Both amplifications suggest higher levels of DISC1 expression in HeLa cells than in lymphoblasts.
Figure 11:
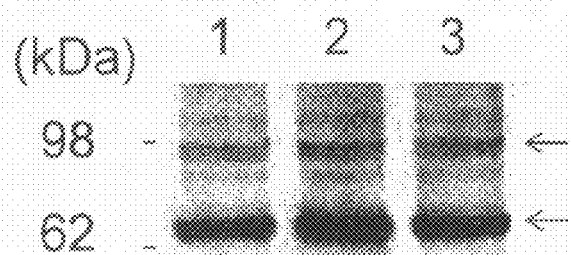
Figure 13:
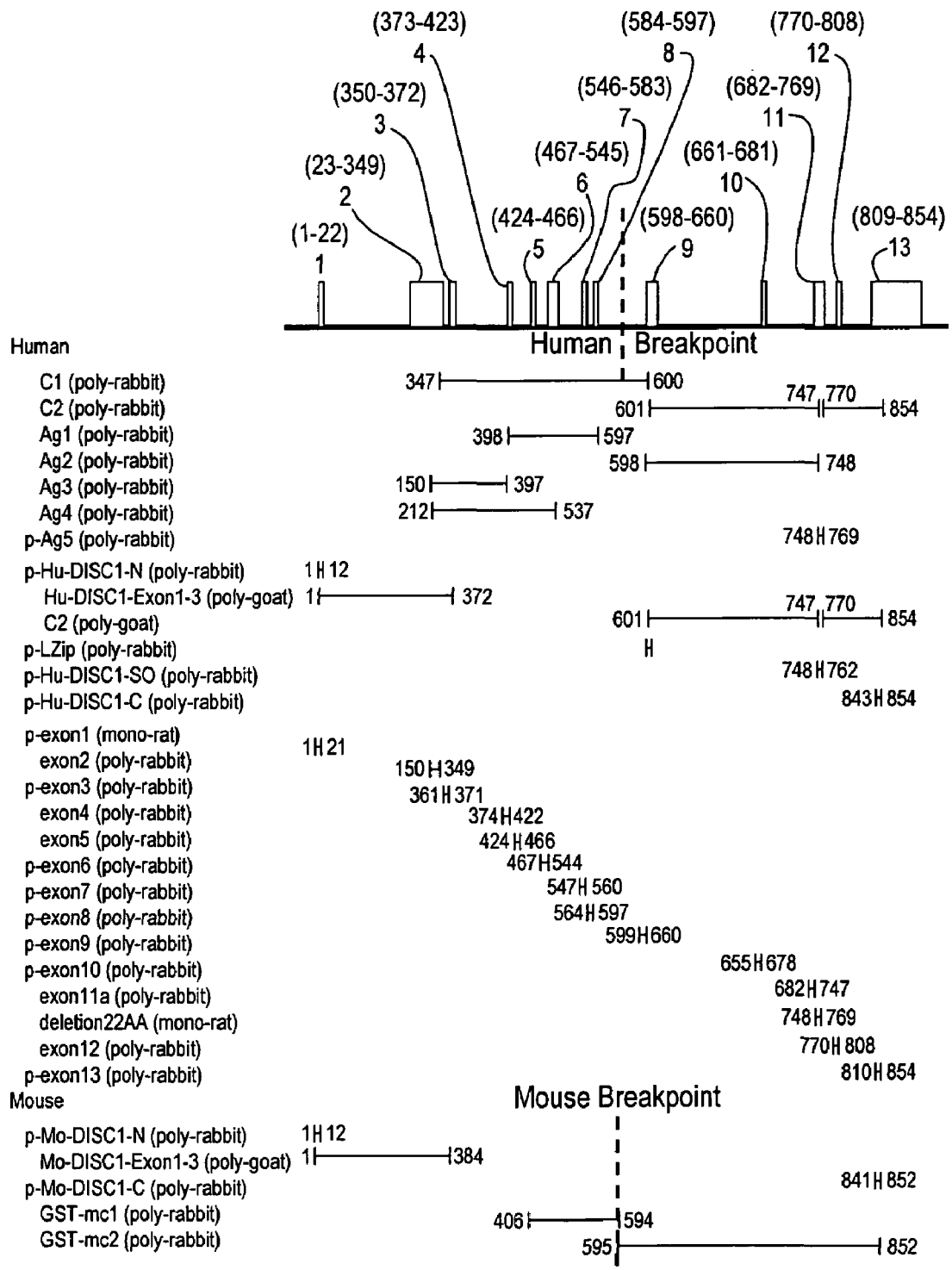
FIG. 13 Antibodies against human and rodent DISC1

First, we examined expression of DISC1 in human lymphoblasts. DISC1 mRNA was addressed by reverse-transcriptase coupled PCR (RT-PCR). Two sets of primer pair were chosen from exons 4 and 5 as well as exon 8 and 9 of DISC1 gene (Table 3C). The primer selection over two independent exons can exclude contaminated signals from genomic DNA. In both amplifications, the specific signals were obtained from both HeLa cells and human lymphoblasts with a consistently lower intensity from lymphoblasts (FIG. 11A). DISC1 protein was analyzed in Western blotting by using well-characterized anti-DISC1 antibodies with independent epitopes (Ozeki et al 2003). We obtained major signal(s) at approximately 70-80 kDa, with weaker signal(s) at 90-95 kDa (FIG. 11B) an expression pattern similar to rat and human adult brains (Brandon et al 2004; Miyoshi et al 2003; Ozeki et al 2003).

Second, based on the expression profiles of DISC1 in lymphoblasts similar to those in adult brains, we examined the relationship of DISC1 haplotypes to its expression levels. Expression of DISC1 in lymphoblasts from affected subjects with the risk haplotype (HP1) (16 cases) was compared with that from unaffected family members with the under-transmitted haplotype (HP2) (11 controls). Levels of DISC1 are significantly lower in bipolar subjects with HP1 than unaffected relatives with HP2 (p=0.006) (FIG. 12A). The consistent gender influence, as observed in the transmission, exists with more remarkable suppression in females (p=0.001) (FIG. 12B). The semi-quantitative assessment of DISC1 by real-time PCR as well as Western blotting confirms this observation (data not shown).

4.3 Clinical Data Analysis

Of all the clinical features, the number of manic episodes correlates most with the decreased levels of DISC1 expression (coefficient of correlation, −0.41; p=0.008) (Table 5). Earlier age of first manic episode also tends to correlate with lower DISC1 expression. In addition, age of first hospitalization seems to correlate negatively with DISC1 expression when other factors are controlled for. Other features, including psychosis, show no significant correlation when all other factors are controlled for.

TABLE 5

Linear regression of DISC 1 expression in relation to severity measures of mania in the clinical data of study subjects

| MEASURES | COEFFICIENT | STD ERROR[a] | z[b] | p[c] |
|---|---|---|---|---|
| Number of manic symptoms | −0.41 | 0.15 | −2.64 | 0.008 |
| Age of 1$^{st}$ episode | 0.24 | 0.13 | 1.92 | 0.06 |
| Number of manic episodes | −0.03 | 0.01 | −1.92 | 0.06 |
| Age of 1$^{st}$ hospitalization | −0.27 | 0.12 | −2.2 | 0.03 |

[a]standard error
[b]z distribution
[c]p value

REFERENCES

References shown below are herein incorporated by reference:

1 Ahmad, F. J., Echeverri, C. J., Vallee, R. B., and Baas, P. W. (1998). Cytoplasmic dynein and dynactin are required for the transport of microtubules into the axon. J Cell Biol 140, 391-401.

2 Akbarian, S., Bunney, W. E., Jr., Potkin, S. G., Wigal, S. B., Hagman, J. O., Sandman, C. A., and Jones, E. G. (1993). Altered distribution of nicotinamide-adenine dinucleotide phosphate-diaphorase cells in frontal lobe of schizophrenics implies disturbances of cortical development. Arch Gen Psychiatry 50, 169-177.

3 Andrews, N.C. & Faller, D. V. (1991) Nucleic Acids Res 19, 2499.

4 Arnold S E, Han L Y, Moberg P J, Turetsky B I, Gur R E, Trojanowski J Q, Hahn C G., Arch Gen Psychiatry. 2001 September; 58(9):829-35.

5 Austin C P, Ky B, Ma L, Morris J A, Shughrue P J (2004): Expression of Disrupted-In-Schizophrenia-1, a schizophrenia-associated gene, is prominent in the mouse hippocampus throughout brain development. Neuroscience 124:3-10.

6 Austin C P, Ma L, Ky B, Morris J A, Shughrue P J (2003): DISC1 (Disrupted in Schizophrenia-1) is expressed in limbic regions of the primate brain. Neuroreport 14:951-954.

7 Bechara, A., Damasio, H. & Damasio, A. R. (2000) Cereb Cortex-10, 295-307.

8 Berrettini W H (2000a): Are schizophrenic and bipolar disorders related? A review of family and molecular studies. Biol Psychiatry 48:531-538.

9 Berrettini W H (2000b): Susceptibility loci for bipolar disorder: overlap with inherited vulnerability to schizophrenia. Biol Psychiatry 47:245-251.

10 Blackwood D H, Fordyce A, Walker M T, St Clair D M, Porteous D J, Muir W J (2001): Schizophrenia and affective disorders—cosegregation with a translocation at chromosome 1q42 that directly disrupts brain-expressed genes: clinical and P300 findings in a family. Am J Hum Genet 69:428-433.

11 Blackwood, D. H., Fordyce, A., Walker, M. T., St Clair, D. M., Porteous, D. J. & Muir, W. J. (2001) Am J Hum Genet 69, 428-433.

12 Brandon N J, Handford E J, Schurov I, Rain J C, Pelling M, Duran-Jimeniz B, et al (2004): Disrupted in Schizophrenia 1 and Nudel form a neurodevelopmentally regulated protein complex: implications for schizophrenia and other major neurological disorders. Mol Cell Neurosci 25:42-55.

13 Brandon, N.J., Handford, E. J., Schurov, I., Rain, J. C., Pelling, M., Duran-Jimeniz, B., Camargo, L. M., Oliver, K. R., Beher, D., Shearman, M. S., et al. (2004) Mol Cell Neurosci 25, 42-55.

14 Cheung V G, Conlin L K, Weber T M, Arcaro M, Jen K Y, Morley M, et al (2003): Natural variation in human gene expression assessed in lymphoblastoid cells. Nat Genet 33:422-425.

15 Coyle J T, Duman R S (2003): Finding the intracellular signaling pathways affected by mood disorder treatments. Neuron 38:157-160.

16 Crews L, Hunter D., Perspect Dev Neurobiol. 1994;2(2): 151-61.

17 Curtis D, Kalsi G, Brynjolfsson J, McInnis M, O'Neill J, Smyth C, et al (2003): Genome scan of pedigrees multiply affected with bipolar disorder provides further support for the presence of a susceptibility locus on chromosome 12q23q24, and suggests the presence of additional loci on 1p and 1q. Psychiatr Genet 13:77-84.

18 Detera-Wadleigh S D, Badner J A, Berrettini W H, Yoshikawa T, Goldin L R, Turner G, et al (1999): A high density genome scan detects evidence for a bipolar-disorder susceptibility locus on 13q32 and other potential loci on 1q32 and 18p11.2. Proc Natl Acad Sci USA 96:5604-5609.

19 Ekelund J, Hennah W, Hiekkalinna T, Parker A, Meyer J, Lonnqvist J, et al (2004): Replication of 1q42 linkage in Finnish schizophrenia pedigrees. Mol Psychiatry.

20 Ekelund J, Hovatta I, Parker A, Paunio T, Varilo T, Martin R, et al (2001): Chromosome 1 loci in Finnish schizophrenia families. Hum Mol Genet 10:1611-1617.

21 Emamian, E. S., Hall, D., Birnbaum, M. J., Karayiorgou, M. & Gogos, J. A. (2004) Nat Genet 36, 131-137.

22 Farbman A I., Semin Cell Biol. 1994 February; 5(1):3-10. Review.

23 Feron F, Perry C, Hirning M H, McGrath J, Mackay-Sim A., Schizophr Res. 1999 Dec. 21; 40(3):211-8.

24 Gabriel S B, Schaffner S F, Nguyen H, Moore J M, Roy J, Blumenstiel B, et al (2002): The structure of haplotype blocks in the human genome. Science 296:2225-2229.

25 Gu, Y., Misonou, H., Sato, T., Dohmae, N., Takio, K. & Ihara, Y. (2001) J Biol Chem 276, 35235-35238.

26 Harrison, P. J. & Weinberger, D. R. (2004) Mol Psychiatry.

27 Hennah W, Varilo T, Kestila M, Paunio T, Arajarvi R, Haukka J, et al (2003): Haplotype transmission analysis provides evidence of association for DISC1 to schizophrenia and suggests sex-dependent effects. Hum Mol Genet 12:3151-3159.

28 Hodgkinson C A, Goldman D, Jaeger J, Persaud S, Kane J M, Lipsky R H, et al (2004): Disrupted in Schizophrenia 1 (DISC1): Association with Schizophrenia, Schizoaffective Disorder, and Bipolar Disorder. Am J Hum Genet 75:862-872.

29 Horvath S, Xu X, Laird N M (2001): The family based association test method: strategies for studying general genotype—phenotype associations. Eur J Hum Genet 9:301-306.

30 Hua, X., Sakai, J., Brown, M. S. & Goldstein, J. L. (1996) *J Biol Chem* 271, 10379-10384.

31 Hwu H G, Liu C M, Fann C S, Ou-Yang W C, Lee S F (2003): Linkage of schizophrenia with chromosome 1q loci in Taiwanese families. Mol Psychiatry 8:445-452.

32 James, R., Adams, R. R., Christie, S., Buchanan, S. R., Porteous, D. J. & Millar, J. K. (2004) *Mol Cell Neurosci* 26, 112-122.

33 Knable, M. B. (1999) Schizophr Res 39, 149-152; discussion 163.

34 Koh, P. O., Bergson, C., Undie, A. S., Goldman-Rakic, P. S. & Lidow, M. S. (2003) Arch Gen Psychiatry 60, 311-319.

35 Koh, P. O., Undie, A. S., Kabbani, N., Levenson, R., Goldman-Rakic, P. S. & Lidow, M. S. (2003) Proc Natl Acad Sci USA 100, 313-317.

36 Kringelbach, M. L. & Rolls, E. T. (2004) Prog Neurobiol 72, 341-372.

37 London, E. D., Ernst, M., Grant, S., Bonson, K. & Weinstein, A. (2000) Cereb Cortex 10, 334-342.

38 Ma, L., Liu, Y., Ky, B., Shughrue, P. J., Austin, C. P. & Morris, J. A. (2002) *Genomics* 80, 662-672.

39 Macgregor S, Visscher P M, Knott S A, Thomson P, Porteous D J, Millar J K, et al (2004): A genome scan and follow-up study identify a bipolar disorder susceptibility locus on chromosome 1q42. Mol Psychiatry.

40 McInnis M G, Lan T H, Willour V L, McMahon F J, Simpson S G, Addington A M, et al (2003): Genome-wide scan of bipolar disorder in 65 pedigrees: supportive evidence for linkage at 8q24, 18q22, 4q32, 2p12, and 13q12. Mol Psychiatry 8:288-298.

41 Millar, J. K., Christie, S., and Porteous, D. J. (2003). Yeast two-hybrid screens implicate DISC1 in brain development and function. Biochem Biophys Res Commun 311, 1019-1025.

42 Millar, J. K., Wilson-Annan, J. C., Anderson, S., Christie, S., Taylor, M. S., Semple, C. A., Devon, R. S., Clair, D. M., Muir, W. J., Blackwood, D. H., and Porteous, D. J. (2000). Disruption of two novel genes by a translocation co-segregating with schizophrenia. Hum Mol Genet 9, 1415-1423.

43 Miyoshi K, Honda A, Baba K, Taniguchi M, Oono K, Fujita T, et al (2003): Disrupted-In-Schizophrenia 1, a candidate gene for schizophrenia, participates in neurite outgrowth. Mol Psychiatry 8:685-694.

44 Moberg P J, Agrin R, Gur R E, Gur R C, Turetsky B I, Doty R L., Neuropsychopharmacology. 1999 September; 21(3):325-40.

45 Mohammed, M., and Michel, B. (1998). Method of centrosome isolation from cultured animal cells. In Cell Biology: A Laboratory handbook, J. E. Celis., ed. (San Diego, Calif., Academic Press), pp. 111-119.

46 Morley M, Molony C M, Weber T M, Devlin J L, Ewens K G, Spielman R S, et al (2004): Genetic analysis of genome-wide variation in human gene expression. Nature 430:743-747.

47 Morris J A, Kandpal G, Ma L, Austin C P (2003): DISC1 (Disrupted-In-Schizophrenia 1) is a centrosome-associated protein that interacts with MAP1A, MIPT3, ATF4/5 and NUDEL: regulation and loss of interaction with mutation. Hum Mol Genet 12:1591-1608.

48 Morris, J. A., Kandpal, G., Ma, L., and Austin, C. P. (2003). DISC1 (Disrupted-In-Schizophrenia 1) is a centrosome-associated protein that interacts with MAP1A, MIPT3, ATF4/5 and NUDEL: regulation and loss of interaction with mutation. Hum Mol Genet 12, 1591-1608.

49 Nagata E, Sawa A, Ross C A, Snyder S H (2004): Autophagosome-like vacuole formation in Huntington's disease lymphoblasts. Neuroreport 15:1325-1328.

50 Nakajima, K., Mikoshiba, K., Miyata, T., Kudo, C., and Ogawa, M. (1997). Disruption of hippocampal development in vivo by CR-50 mAb against reelin. Proc Natl Acad Sci USA 94, 8196-8201.

51 Niethammer, M., Smith, D. S., Ayala, R., Peng, J., Ko, J., Lee, M. S., Morabito, M., and Tsai, L. H. (2000). NUDEL is a novel Cdk5 substrate that associates with LIS1 and cytoplasmic dynein. Neuron 28, 697-711.

52 Niwa, H., Yamamura, K., and Miyazaki, J. (1991). Efficient selection for high-expression transfectants with a novel eukaryotic vector. Gene 108, 193-199.

53 Ozeki, Y., Tomoda, T., Kleiderlein, J., Kamiya, A., Bord, L., Fujii, K., Okawa, M., Yamada, N., Hatten, M. E., Snyder, S. H., et al. (2003). Disrupted-in-Schizophrenia-1 (DISC-1): mutant truncation prevents binding to NudE-like (NUDEL) and inhibits neurite outgrowth. Proc Natl Acad Sci USA 100, 289-294.

54 Panov A V, Gutekunst C A, Leavitt B R, Hayden M R, Burke J R, Strittmatter W J, Greenamyre J T., Nat Neurosci. 2002 August; 5(8):731-6.

55 Porrino, L. J. & Lyons, D. (2000) Cereb Cortex 10, 326-333.

56 Rabbitts, T. H. (1994). Chromosomal translocations in human cancer. Nature 372, 143-149.

57 Reiner, O., Carrozzo, R., Shen, Y., Wehnert, M., Faustinella, F., Dobyns, W. B., Caskey, C. T., and Ledbetter, D. H. (1993). Isolation of a Miller-Dieker lissencephaly gene containing G protein beta-subunit-like repeats. Nature 364, 717-721.

58 Rolls, E. T. (2000) Cereb Cortex 10, 284-294.

59 Ross, M. E., and Walsh, C. A. (2001). Human brain malformations and their lessons for neuronal migration. Annu Rev Neurosci 24, 1041-1070.

60 Sasaki, S., Shionoya, A., Ishida, M., Gambello, M. J., Yingling, J., Wynshaw-Boris, A., and Hirotsune, S. (2000). A LIS1/NUDEL/cytoplasmic dynein heavy chain complex in the developing and adult nervous system. Neuron 28, 681-696.

61 Sawa A, Oyama F, Cairns N J, Amano N, Matsushita M (1997): Aberrant expression of bcl-2 gene family in Down's syndrome brains. Brain Res Mol Brain Res 48:53-59.

62 Sawa, A., and Snyder, S. H. (2002). Schizophrenia: diverse approaches to a complex disease. Science 296, 692-695.

63 Sawa, A., Khan, A. A., Hester, L. D., and Snyder, S. H. (1997). Glyceraldehyde-3-phosphate dehydrogenase: nuclear translocation participates in neuronal and nonneuronal cell death. Proc Natl Acad Sci USA 94, 11669-11674.

64 Sawa, A., Wiegand, G. W., Cooper, J., Margolis, R. L., Sharp, A. H., Lawler, J. F., Jr., Greenamyre, J. T., Snyder, S. H., and Ross, C. A. (1999). Increased apoptosis of Huntington disease lymphoblasts associated with repeat length-dependent mitochondrial depolarization. Nat Med 5, 1194-1198.

65 Sawamura, N., Gong, J. S., Garver, W. S., Heidenreich, R. A., Ninomiya, H., Ohno, K., Yanagisawa, K. & Michikawa, M. (2001) J Biol Chem 276, 10314-10319.

66 Sawamura, N., Ko, M., Yu, W., Zou, K., Hanada, K., Suzuki, T., Gong, J. S., Yanagisawa, K. & Michikawa, M. (2004) J Biol Chem 279, 11984-11991.

67 Schurov I L, Handford E J, Brandon N J, Whiting P J (2004): Expression of disrupted in schizophrenia 1 (DISC1) protein in the adult and developing mouse brain indicates its role in neurodevelopment. Mol Psychiatry.

68 Selemon, L. D., and Goldman-Rakic, P. S. (1999). The reduced neuropil hypothesis: a circuit based model of schizophrenia. Biol Psychiatry 45, 17-25.

69 Smith, D. S., Niethammer, M., Ayala, R., Zhou, Y., Gambello, M. J., Wynshaw-Boris, A., and Tsai, L. H. (2000). Regulation of cytoplasmic dynein behaviour and microtubule organization by mammalian Lis1. Nat Cell Biol 2, 767-775.

70 St Clair, D., Blackwood, D., Muir, W., Carothers, A., Walker, M., Spowart, G., Gosden, C. & Evans, H. J. (1990) Lancet 336, 13-16.

71 Sudoh, S., Kawamura, Y., Sato, S., Wang, R., Saido, T. C., Oyama, F., Sakaki, Y., Komano, H. & Yanagisawa, K. (1998) J Neurochem 71, 1535-1543.

72 Tabata, H., and Nakajima, K. (2001). Efficient in utero gene transfer system to the developing mouse brain using electroporation: visualization of neuronal migration in the developing cortex. Neuroscience 103, 865-872.

73 Taylor, M. S., Devon, R. S., Millar, J. K. & Porteous, D. J. (2003) Genomics 81, 67-77.

74 Tkachev, D., Mimmack, M. L., Ryan, M. M., Wayland, M., Freeman, T., Jones, P. B., Starkey, M., Webster, M. J., Yolken, R. H. & Bahn, S. (2003) Lancet 362, 798-805.

75 Tomoda, T., Kim, J. H., Zhan, C., and Hatten, M. E. (2004). Role of Unc51.1 and its binding partners in CNS axon outgrowth. Genes Dev 18, 541-558.

76 Torrey, E. F. (1999). Epidemiological comparison of schizophrenia and bipolar disorder. Schizophr Res 39, 101-106.

77 Torrey, E. F., Webster, M., Knable, M., Johnston, N. & Yolken, R. H. (2000) Schizophr Res 44, 151-155.

78 Volkow, N. D. & Fowler, J. S. (2000) Cereb Cortex 10, 318-325.

79 Waterman-Storer, C. M., Karki, S. B., Kuznetsov, S. A., Tabb, J. S., Weiss, D. G., Langford, G. M., and Holzbaur, E. L. (1997). The interaction between cytoplasmic dynein and dynactin is required for fast axonal transport. Proc Natl Acad Sci USA 94, 12180-12185.

80 Weinberger, D. R. (1987). Implications of normal brain development for the pathogenesis of schizophrenia. Arch Gen Psychiatry 44, 6.60-669.

81 Xie, Z., Sanada, K., Samuels, B. A., Shih, H., and Tsai, L. H. (2003). Serine 732 phosphorylation of FAK by Cdk5 is important for microtubule organization, nuclear movement, and neuronal migration. Cell 114, 469-482.

82 Yu, J. Y., DeRuiter, S. L., and Turner, D. L. (2002). RNA interference by expression of short-interfering RNAs and hairpin RNAs in mammalian cells. Proc Natl Acad Sci U S A 99, 6047-6052.

1 Ahmad, F. J., Echeverri, C. J., Vallee, R. B., and Baas, P. W. (1998). Cytoplasmic dynein and dynactin are required for the transport of microtubules into the axon. J Cell Biol 140, 391-401.

2 Akbarian, S., Bunney, W. E., Jr., Potkin, S. G., Wigal, S. B., Hagman, J. O., Sandman, C. A., and Jones, E. G. (1993). Altered distribution of nicotinamide-adenine dinucleotide phosphate-diaphorase cells in frontal lobe of schizophrenics implies disturbances of cortical development. Arch Gen Psychiatry 50, 169-177.

3 Andrews, N.C. & Faller, D. V. (1991) Nucleic Acids Res 19, 2499.

4 Austin C P, Ky B, Ma L, Morris J A, Shughrue P J (2004): Expression of Disrupted-In-Schizophrenia-1, a schizophrenia-associated gene, is prominent in the mouse hippocampus throughout brain development. Neuroscience 124:3-10.

5 Austin C P, Ma L, Ky B, Morris J A, Shughrue P J (2003): DISC1 (Disrupted in Schizophrenia-1) is expressed in limbic regions of the primate brain. Neuroreport 14:951-954.

6 Bechara, A., Damasio, H. & Damasio, A. R. (2000) Cereb Cortex 10, 295-307.

7 Berrettini W H (2000a): Are schizophrenic and bipolar disorders related? A review of family and molecular studies. Biol Psychiatry 48:531-538.

8 Berrettini W H (2000b): Susceptibility loci for bipolar disorder: overlap with inherited vulnerability to schizophrenia. Biol Psychiatry 47:245-251.

9 Blackwood D H, Fordyce A, Walker M T, St Clair D M, Porteous D J, Muir W J (2001): Schizophrenia and affective disorders—cosegregation with a translocation at chromosome 1q42 that directly disrupts brain-expressed genes: clinical and P300 findings in a family. Am J Hum Genet 69:428-433.

10 Blackwood, D. H., Fordyce, A., Walker, M. T., St Clair, D. M., Porteous, D. J. & Muir, W. J. (2001) Am J Hum Genet 69, 428-433.

11 Brandon N J, Handford E J, Schurov I, Rain J C, Pelling M, Duran-Jimeniz B, et al (2004): Disrupted in Schizophrenia 1 and Nudel form a neurodevelopmentally regulated protein complex: implications for schizophrenia and other major neurological disorders. Mol Cell Neurosci 25:42-55.

12 Brandon, N.J., Handford, E. J., Schurov, I., Rain, J. C., Pelling, M., Duran-Jimeniz, B., Camargo, L. M., Oliver, K. R., Beher, D., Shearman, M. S., et al. (2004) Mol Cell Neurosci 25, 42-55.

13 Cheung V G, Conlin L K, Weber T M, Arcaro M, Jen K Y, Morley M, et al (2003): Natural variation in human gene expression assessed in lymphoblastoid cells. Nat Genet 33:422-425.

14 Coyle J T, Duman R S (2003): Finding the intracellular signaling pathways affected by mood disorder treatments. Neuron 38:157-160.

15 Curtis D, Kalsi G, Brynjolfsson J, McInnis M, O'Neill J, Smyth C, et al (2003): Genome scan of pedigrees multiply affected with bipolar disorder provides further support for the presence of a susceptibility locus on chromosome 12q23q24, and suggests the presence of additional loci on 1p and 1q. Psychiatr Genet 13:77-84.

16. Detera-Wadleigh S D, Badner J A, Berrettini W H, Yoshikawa T, Goldin L R, Turner G, et al (1999): A high density genome scan detects evidence for a bipolar-disorder susceptibility locus on 13q32 and other potential loci on 1q32 and 18p11.2. Proc Natl Acad Sci USA 96:5604-5609.

17. Ekelund J, Hennah W, Hiekkalinna T, Parker A, Meyer J, Lonnqvist J, et al (2004): Replication of 1q42 linkage in Finnish schizophrenia pedigrees. Mol Psychiatry.

18. Ekelund J, Hovatta I, Parker A, Paunio T, Varilo T, Martin R, et al (2001): Chromosome 1 loci in Finnish schizophrenia families. Hum Mol Genet 10:1611-1617.

19. Emamian, E. S., Hall, D., Birnbaum, M. J., Karayiorgou, M. & Gogos, J. A. (2004) Nat Genet 36, 131-137.

20. Gabriel SB, Schaffner SF, Nguyen H, Moore JM, Roy J, Blumenstiel B, et al (2002): The structure of haplotype blocks in the human genome. Science 296:2225-2229.

21. Gu, Y., Misonou, H., Sato, T., Dohmae, N., Takio, K. & Ihara, Y. (2001) *J Biol Chem* 276, 35235-35238.

22. Harrison, P. J. & Weinberger, D. R. (2004) *Mol Psychiatry.*

23. Hennah W, Varilo T, Kestila M, Paunio T, Arajarvi R, Haukka J, et al (2003): Haplotype transmission analysis provides evidence of association for DISC1 to schizophrenia and suggests sex-dependent effects. Hum Mol Genet 12:3151-3159.

24. Hodgkinson C A, Goldman D, Jaeger J, Persaud S, Kane J M, Lipsky R H, et al (2004): Disrupted in Schizophrenia 1 (DISC1): Association with Schizophrenia, Schizoaffective Disorder, and Bipolar Disorder. Am J Hum Genet 75:862-872.

25. Horvath S, Xu X, Laird N M (2001): The family based association test method: strategies for studying general genotype—phenotype associations. Eur J Hum Genet 9:301-306.

26. Hua, X., Sakai, J., Brown, M. S. & Goldstein, J. L. (1996) *J Biol. Chem.* 271, 10379-10384.

27. Hwu H G, Liu C M, Fann C S, Ou-Yang W C, Lee S F (2003): Linkage of schizophrenia with chromosome 1q loci in Taiwanese families. Mol Psychiatry 8:445-452.

28. James, R., Adams, R. R., Christie, S., Buchanan, S. R., Porteous, D. J. & Millar, J. K. (2004) *Mol Cell Neurosci* 26, 112-122.

29. Knable, M. B. (1999) Schizophr Res 39, 149-152; discussion 163.

30. Koh, P. O., Bergson, C., Undie, A. S., Goldman-Rakic, P. S. & Lidow, M. S. (2003) Arch Gen Psychiatry 60, 311-319.

31. Koh, P. O., Undie, A. S., Kabbani, N., Levenson, R., Goldman-Rakic, P. S. & Lidow, M. S. (2003) Proc Natl Acad Sci USA 100, 313-317.

32. Kringelbach, M. L. & Rolls, E. T. (2004) Prog Neurobiol 72, 341-372.

33. London, E. D., Ernst, M., Grant, S., Bonson, K. & Weinstein, A. (2000) Cereb Cortex 10, 334-342.

34. Ma, L., Liu, Y., Ky, B., Shughrue, P. J., Austin, C. P. & Morris, J. A. (2002) *Genomics* 80, 662-672.

35. Macgregor S, Visscher P M, Knott S A, Thomson P, Porteous D J, Millar J K, et al (2004): A genome scan and follow-up study identify a bipolar disorder susceptibility locus on chromosome 1q42. Mol Psychiatry.

36. McInnis MG, Lan T H, Willour V L, McMahon F J, Simpson S G, Addington A M, et al (2003): Genome-wide scan of bipolar disorder in 65 pedigrees: supportive evidence for linkage at 8q24, 18q22, 4q32, 2p12, and 13q12. Mol Psychiatry 8:288-298.

37. Millar, J. K., Christie, S., and Porteous, D. J. (2003). Yeast two-hybrid screens implicate DISC1 in brain development and function. Biochem Biophys Res Commun 311, 1019-1025.

38. Millar, J. K., Wilson-Annan, J. C., Anderson, S., Christie, S., Taylor, M. S., Semple, C. A., Devon, R. S., Clair, D. M., Muir, W. J., Blackwood, D. H., and Porteous, D. J. (2000). Disruption of two novel genes by a translocation co-segregating with schizophrenia. Hum Mol Genet 9, 1415-1423.

39. Miyoshi K, Honda A, Baba K, Taniguchi M, Oono K, Fujita T, et al (2003): Disrupted-In-Schizophrenia 1, a candidate gene for schizophrenia, participates in neurite outgrowth. Mol Psychiatry 8:685-694.

40. Mohammed, M., and Michel, B. (1998). Method of centrosome isolation from cultured animal cells. In Cell Biology: A Laboratory handbook, J. E. Celis., ed. (San Diego, Calif., Academic Press), pp. 111-119.

41. Morley M, Molony C M, Weber T M, Devlin J L, Ewens K G, Spielman R S, et al (2004): Genetic analysis of genome-wide variation in human gene expression. Nature 430:743-747.

42. Morris J A, Kandpal G, Ma L, Austin C P (2003): DISC1 (Disrupted-In-Schizophrenia 1) is a centrosome-associated protein that interacts with MAP1A, MIPT3, ATF4/5 and NUDEL: regulation and loss of interaction with mutation. Hum Mol Genet 12:1591-1608.

43. Morris, J. A., Kandpal, G., Ma, L., and Austin, C. P. (2003). DISC1 (Disrupted-In-Schizophrenia 1) is a centrosome-associated protein that interacts with MAP1A, MIPT3, ATF4/5 and NUDEL: regulation and loss of interaction with mutation. Hum Mol Genet 12, 1591-1608.

44. Nagata E, Sawa A, Ross C A, Snyder S H (2004): Autophagosome-like vacuole formation in Huntington's disease lymphoblasts. Neuroreport 15:1325-1328.

45. Nakajima, K., Mikoshiba, K., Miyata, T., Kudo, C., and Ogawa, M. (1997). Disruption of hippocampal development in vivo by CR-50 mAb against reelin. Proc Natl Acad Sci USA 94, 8196-8201.

46. Niethammer, M., Smith, D. S., Ayala, R., Peng, J., Ko, J., Lee, M. S., Morabito, M., and Tsai, L. H. (2000). NUDEL is a novel Cdk5 substrate that associates with LIS1 and cytoplasmic dynein. Neuron 28, 697-711.

47. Niwa, H., Yamamura, K., and Miyazaki, J. (1991). Efficient selection for high-expression transfectants with a novel eukaryotic vector. Gene 108, 193-199.

48. Ozeki, Y., Tomoda, T., Kleiderlein, J., Kamiya, A., Bord, L., Fujii, K., Okawa, M., Yamada, N., Hatten, M. E., Snyder, S. H., et al. (2003). Disrupted-in-Schizophrenia-1 (DISC-1): mutant truncation prevents binding to NudE-like (NUDEL) and inhibits neurite outgrowth. Proc Natl Acad Sci USA 100, 289-294.

49. Porrino, L. J. & Lyons, D. (2000) Cereb Cortex 10, 326-333.

50. Rabbitts, T. H. (1994). Chromosomal translocations in human cancer. Nature 372, 143-149.

51. Reiner, O., Carrozzo, R., Shen, Y., Wehnert, M., Faustinella, F., Dobyns, W. B., Caskey, C. T., and Ledbetter, D. H. (1993). Isolation of a Miller-Dieker lissencephaly gene containing G protein beta-subunit-like repeats. Nature 364, 717-721.

52. Rolls, E. T. (2000) Cereb Cortex 10, 284-294.

53. Ross, M. E., and Walsh, C. A. (2001). Human brain malformations and their lessons for neuronal migration. Annu Rev Neurosci 24, 1041-1070.

54. Sasaki, S., Shionoya, A., Ishida, M., Gambello, M. J., Yingling, J., Wynshaw-Boris, A., and Hirotsune, S. (2000).

A LIS1/NUDEL/cytoplasmic dynein heavy chain complex in the developing and adult nervous system. Neuron 28, 681-696.
55 Sawa A, Oyama F, Cairns N J, Amano N, Matsushita M (1997): Aberrant expression of bcl-2 gene family in Down's syndrome brains. Brain Res Mol Brain Res 48:53-59.
56 Sawa, A., and Snyder, S. H. (2002). Schizophrenia: diverse approaches to a complex disease. Science 296, 692-695.
57 Sawa, A., Khan, A. A., Hester, L. D., and Snyder, S. H. (1997). Glyceraldehyde-3-phosphate dehydrogenase: nuclear translocation participates in neuronal and nonmeuronal cell death. Proc Natl Acad Sci USA 94, 11669-11674.
58 Sawa, A., Wiegand, G. W., Cooper, J., Margolis, R. L., Sharp, A. H., Lawler, J. F., Jr., Greenamyre, J. T., Snyder, S. H., and Ross, C. A. (1999). Increased apoptosis of Huntington disease lymphoblasts associated with repeat length-dependent mitochondrial depolarization. Nat Med 5, 1194-1198.
59 Sawamura, N., Gong, J. S., Garver, W. S., Heidenreich, R. A., Ninomiya, H., Ohno, K., Yanagisawa, K. & Michikawa, M. (2001) J Biol Chem 276, 10314-10319.
60 Sawamura, N., Ko, M., Yu, W., Zou, K., Hanada, K., Suzuki, T., Gong, J. S., Yanagisawa, K. & Michikawa, M. (2004) J Biol Chem 279, 11984-11991.
61 Schurov I L, Handford E J, Brandon N J, Whiting P J (2004): Expression of disrupted in schizophrenia 1 (DISC1) protein in the adult and developing mouse brain indicates its role in neurodevelopment. Mol Psychiatry.
62 Selemon, L. D., and Goldman-Rakic, P. S. (1999). The reduced neuropil hypothesis: a circuit based model of schizophrenia. Biol Psychiatry 45, 17-25.
63 Smith, D. S., Niethammer, M., Ayala, R., Zhou, Y., Gambello, M. J., Wynshaw-Boris, A., and Tsai, L. H. (2000). Regulation of cytoplasmic dynein behaviour and microtubule organization by mammalian Lis1. Nat Cell Biol 2, 767-775.
64 St Clair, D., Blackwood, D., Muir, W., Carothers, A., Walker, M., Spowart, G., Gosden, C. & Evans, H. J. (1990) Lancet 336, 13-16.
65 Sudoh, S., Kawamura, Y., Sato, S., Wang, R., Saido, T. C., Oyama, F., Sakaki, Y., Komano, H. & Yanagisawa, K. (1998) J Neurochem 71, 1535-1543.
66 Tabata, H., and Nakajima, K. (2001). Efficient in utero gene transfer system to the developing mouse brain using electroporation: visualization of neuronal migration in the developing cortex. Neuroscience 103, 865-872.
67 Taylor, M. S., Devon, R. S., Millar, J. K. & Porteous, D. J. (2003) Genomics 81, 67-77.
68 Tkachev, D., Mimmack, M. L., Ryan, M. M., Wayland, M., Freeman, T., Jones, P. B., Starkey, M., Webster, M. J., Yolken, R. H. & Bahn, S. (2003) Lancet 362, 798-805.
69 Tomoda, T., Kim, J. H., Zhan, C., and Hatten M. E. (2004). Role of Unc51.1 and its binding partners in CNS axon outgrowth. Genes Dev 18, 541-558.
70 Torrey, E. F. (1999). Epidemiological comparison of schizophrenia and bipolar disorder. Schizophr Res 39, 101-106.
71 Torrey, E. F., Webster, M., Knable, M., Johnston, N. & Yolken, R. H. (2000) Schizophr Res 44, 151-155.
72 Volkow, N. D. & Fowler, J. S. (2000) Cereb Cortex 10, 318-325.
73 Waterman-Storer, C. M., Karki, S. B., Kuznetsov, S. A., Tabb, J. S., Weiss, D. G., Langford, G. M., and Holzbaur, E. L. (1997). The interaction between cytoplasmic dynein and dynactin is required for fast axonal transport. Proc Natl Acad Sci USA 94, 12180-12185.
74 Weinberger, D. R. (1987). Implications of normal brain development for the pathogenesis of schizophrenia. Arch Gen Psychiatry 44, 660-669.
75 Xie, Z., Sanada, K., Samuels, B. A., Shih, H., and Tsai, L. H. (2003). Serine 732 phosphorylation of FAK by Cdk5 is important for microtubule organization, nuclear movement, and neuronal migration. Cell 114, 469-482.
76 Yu, J. Y., DeRuiter, S. L., and Turner, D. L. (2002). RNA interference by expression of short-interfering RNAs and hairpin RNAs in mammalian cells. Proc Natl Acad Sci U S A 99, 6047-6052.

What is claimed is:

1. A method for diagnosing or predicting susceptibility of an individual to schizophrenia, major depression or substance abuse, which comprises:

determining the subcellular distribution of Disrupted-in Schizophrenia-1 (DISC1) protein in cells from said individual and from an unaffected control individual, wherein said cells are selected from the group consisting of brain cells and lymphoblasts; and wherein an increase in the ratio of nuclear to cytoplasmic amounts of DISC1 protein in the cells from the individual being diagnosed, as compared to the cells from said unaffected control individual, indicates the presence of schizophrenia, major depression or substance abuse, or susceptibility thereto.

2. The method of Claim 1, wherein said DISC1 is detected with an antibody against DISC1 protein.

3. The method of Claim 1, wherein the cells are lymphoblasts.

4. A method for diagnosing or predicting susceptibility of an individual to bipolar disorder, which comprises determining the expression level of DISC 1 protein in lymphoblasts from said individual and from an unaffected control individual, and wherein a decrease in the expression level of DISC1 in the lymphoblasts from the individual being diagnosed, as compared to lymphoblasts from said unaffected control individual, indicates the presence of bipolar disorder or susceptibility thereto.

5. The method of claim 4, wherein said DISC1 is detected with an antibody against DISC1 protein.

* * * * *